US011377699B2

(12) United States Patent
Garnis et al.

(10) Patent No.: US 11,377,699 B2
(45) Date of Patent: Jul. 5, 2022

(54) METHODS FOR EVALUATING HEAD AND NECK CANCERS

(71) Applicant: PROVINCIAL HEALTH SERVICES AUTHORITY, Vancouver (CA)

(72) Inventors: Catherine Garnis, North Vancouver (CA); Martial Guillaud, Gibsons (CA)

(73) Assignee: PROVINCIAL HEALTH SERVICES AUTHORITY, Vancouver (CA)

(*) Notice: Subject to any disclaimer, the term of this patent is extended or adjusted under 35 U.S.C. 154(b) by 5 days.

(21) Appl. No.: 16/767,090

(22) PCT Filed: Nov. 30, 2018

(86) PCT No.: PCT/CA2018/051537
§ 371 (c)(1),
(2) Date: May 26, 2020

(87) PCT Pub. No.: WO2019/104445
PCT Pub. Date: Jun. 6, 2019

(65) Prior Publication Data
US 2020/0370125 A1 Nov. 26, 2020

Related U.S. Application Data

(60) Provisional application No. 62/744,572, filed on Oct. 11, 2018, provisional application No. 62/592,488, filed on Nov. 30, 2017.

(51) Int. Cl.
C12Q 1/6886 (2018.01)

(52) U.S. Cl.
CPC ..... *C12Q 1/6886* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2011/0015080 A1* | 1/2011 | Golub | C12Q 1/6834 506/2 |
| 2012/0108655 A1 | 5/2012 | Avissar et al. | |
| 2014/0120545 A1* | 5/2014 | Umansky | C12Q 1/6886 435/6.12 |
| 2015/0018227 A1* | 1/2015 | Taylor | C12Q 1/6886 506/9 |
| 2016/0024503 A1* | 1/2016 | Kalluri | G16B 20/00 424/1.11 |

FOREIGN PATENT DOCUMENTS

| EP | 3369826 A1 | 9/2018 |
| WO | 2013095132 A1 | 6/2013 |

OTHER PUBLICATIONS

Lajer et al British J Cancer. 2014. 104: 830-840 (Year: 2014).*
Chen et al Redox Biology. 2019. 22: 101140, 11 pages (Year: 2019).*
Yap et al Cancer Prevention Research. 2018. 11(8): 491-502 (Year: 2018).*
Qi et al Medicine. 2021. 100(6). p. 1-10 (Year: 2021).*
MacLellan et al Cancer Medicine. 2012. 1(2): 268-274 and Supporting Information, 2 pages (Year: 2012).*
Zhou et al (cientific Reports. Jun. 10, 2015. 6:11251 (Year: 2015).*
Tumilson et al Molecular Neurobiology. 2014. 50: 545-558 (Year: 2014).*
Min et al BMC Genomics. 2010. 11:96 (Year: 2010).*
Fukumoto et al International J Oncology. 2016. 49: 1119-1129 (Year: 2016).*
MacLellan et al. BMC Clinical Pathology. 2014. 14: 27, pp. 1-11 (Year: 2014).*
Veit et al Anticancer Research. 2015. 35: 1271-1278 (Year: 2015).*
Gu et al Shanghai J Stomatol. 2015. 24(1): 71-75 (Year: 2015).*
Qureshi et al BMC Medical Genomics. 2013. 6 (Suppl 1): 514, p. 1-13 (Year: 2013).*
MacLellan et al. Cancer Research. AACR Annual Meeting Apr. 2012, published Mar. 31, 2012,. Abstract 4131 (Year: 2012).*
Chen et al., "MicroRNA Deregulations in Head and Neck Squamous Cell Carcinomas", Journal of oral & Maxillofacial Research, Apr. 2013, vol. 4 (1), pp. e2, ISSN 2029-283X.
Gonzalez-Arriagada et al.,"Clinicopathological Significance of miR-26, miR-107, miR-125b and miR-203 in Head and Neck Carcinomas," Oral Disease, Sep. 2018, vol. 24 (6), pp. 930-939, ISSN 1601-0825.
International Patent Application No. PCT/CA2018/051537, International Preliminary Reporton Patentability and Written Opinion dated Jun. 11, 2020.
International Patent Application No. PCT/CA2018/051537, International Search Report and Written Opinion dated Feb. 21, 2019.
Jamali et al., "MicroRNAs as Prognostic Molecular Signatures in Human Head and Neck Squamous Cell Carcinoma: A Systematic Review and Meta-Analysis", Oral Oncology, Apr. 2015, vol. 51 (4), pp. 321-331, ISSN 1368-8375.

(Continued)

*Primary Examiner* — Carla J Myers
(74) *Attorney, Agent, or Firm* — Borden Ladner Gervais LLP; Michael Damiani

(57) ABSTRACT

The present disclosure provides a method for diagnosing a head and neck cancer in a subject. The method comprises the steps of: a) measuring an expression level of miR-125b or miR-342 and miR-125b in a sample from the subject; b) measuring an expression level of a normalizing miR in the sample and normalizing the measured expression level of miR-125b or miR-342 and miR-125b using the measured expression level of the normalizing miR; and c) diagnosing a head and neck cancer in a subject having a normalized measured expression level of miR-125b elevated relative to a reference expression level of miR-125b or having a ratio of normalized measured expression level of miR-342 to normalized measured expression level of miR-125b reduced relative to a reference ratio of expression level of miR-342 to expression level of miR-125b. Uses and kits associated with the herein disclosed methods are also disclosed.

10 Claims, 9 Drawing Sheets

Specification includes a Sequence Listing.

(56) References Cited

OTHER PUBLICATIONS

Khawar et al., "Head and Neck Cancer Diagnosis and Management of", Head and Neck Cancer: Epidemiology and Role of MicroRNAs, Sep. 6, 2017, ISBN 978-953-51-3496-1 (online) (retrieved on Jan. 28, 2019 (Jan. 28, 2019)).
Peng et al., "MicroRNAs MiR-218, MiR-125b, and Let-7g Predict Prognosis in Patients with Oral Cavity Squamous Cell Carcinoma", PLoS One, Jul. 2014, vol. 9 (7), pp. e102403, ISSN 1932-6203.
Shiiba et al., "MicroRNA-125b Regulates Proliferation and Radio Resistance of Oral Squamous Cell Carcinoma", British Journal of Cancer, May 2013, vol. 108(9), pp. 1817-1821, ISSN 1532-1827.
Canadian Patent Application No. 3,083,140, Office Action dated Jul. 7, 2021.
Gu et al., "Expression and Clinical Significance of Plasma MicroRNA-125b Level in Patients With Oral Squamous Cell Carcinoma" Shanghai Kou Qiang Yi Xue, Feb. 2015, vol. 24(1), pp. 71-75. (Abstract), 1 page.
European Patent Application No. 18883957.5, Extended European Search Report dated Sep. 27, 2021.
Roberts et al., "miRCURY LNA Research Tools for MicroRNA," Nature Methods, Sep. 2006, vol. 9(3), XP002471881, ISSN: 1548-7091, 2 pages.

\* cited by examiner

METHODS FOR EVALUATING HEAD AND NECK CANCERS

CROSS REFERENCE TO RELATED APPLICATIONS

This application claims the benefit of priority of U.S. Provisional Patent Application Nos. 62/592,488, filed Nov. 30, 2017, and 62/744,572, filed Oct. 11, 2018, which are hereby incorporated by reference.

FIELD

The present disclosure relates generally to methods for evaluating head and neck cancers.

BACKGROUND

The following paragraph is not an admission that anything discussed in it is prior art or part of the knowledge of persons skilled in the art.

Head and neck cancer is the 6$^{th}$ most common cancer worldwide, of which oral squamous cell carcinoma is the most prevalent subtype with about 50,000 new cases in North America each year. Mortality rates for oral cancer (OC) are high, largely due to frequent late stage diagnosis and high rates of recurrence. The 5-year recurrence rate for OC is about 50% with the majority recurring in less than 2 years (Carvalho, A. L. et a. Treatment results on advanced neck metastasis (N3) from head and neck squamous carcinoma. *Otolaryngol Head Neck Surg* 132, 862-868 (2005)). Despite advances in treatment, overall survival rates of this disease have not changed for decades.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

One or more known methods used for detecting and/or analyzing head and neck cancers may: (1) detect new occurrences of head and neck cancer at an insufficiently early disease stage; (2) detect reoccurrence of head and neck cancer at an insufficiently early disease stage; or (3) a combination thereof. For example, one or more known methods utilize a 'watchful waiting' standard of care for post-treatment oral cancer patients where patients receive clinical exams at 3-6 months intervals post treatment. However, due to scar tissue resulting from initial treatment, it is difficult to detect recurrent disease by clinical exam. Reoccurring disease is often only diagnosed when patients exhibit new symptoms, for example, bleeding, pain, etc. Accordingly, the majority of reoccurring cases have progressed to metastasis at the time of diagnosis leaving limited treatment options available. Furthermore, currently used post-treatment imaging methods, for example, CT, PET, and CT/PET scans, may be prone to false positives, require undesirable radiation exposure, be inaccessible, be costly, or a combination thereof. Accordingly, currently used post-treatment imaging methods are not routinely used for long-term follow-up protocols.

The authors of the present disclosure addressed one or more of the drawbacks associated with one or more known methods used for detecting, and/or analyzing head and neck cancers by developing methods that use a microRNA (miRNA) signature comprising miR-125b or miR-125b and miR-342. The present invention allows for more desirable methods of predicting, detecting and/or analyzing head and neck cancer in a subject compared to one or more known methods that do not utilize miR-125b or miR-125b and miR-342. One or more methods according to the present disclosure may: (1) predict, detect, and/or analyze an initial occurrence of head and neck cancer in a subject at an earlier disease stage than one or more known methods; (2) predict, detect, and/or analyze a reoccurrence of head and neck cancer in a subject at an earlier disease stage than one or more known methods; (3) decrease the invasiveness of predicting, detecting, and/or analyzing head and neck cancer compared to the one or more known methods; (4) predict, detect, and/or analyze head and neck cancer more accurately than one or more known methods; or (5) a combination thereof. As a result, the present disclosure may allow for a wider range of prevention and/or treatment options available for a subject, which may increase subject survival rates.

Uses and kits associated with the herein disclosed methods of predicting, detecting, and/or analyzing head and neck cancers are also disclosed.

In one aspect, the present disclosure provides a method for predicting an increase in the likelihood of a head and neck cancer developing in a subject, the method comprising the steps of: a) measuring an expression level of miR-125b in a sample from the subject; b) measuring an expression level of a normalizing miR in the sample and normalizing the measured expression level of miR-125b using the measured expression level of the normalizing miR; and c) predicting an increase in the likelihood of a head and neck cancer developing in a subject having a normalized measured expression level of miR-125b elevated relative to a reference expression level of miR-125b.

In another aspect, the present disclosure provides a method for diagnosing a head and neck cancer in a subject, the method comprising the steps of: a) measuring an expression level of miR-125b in a sample from the subject; b) measuring an expression level of a normalizing miR in the sample and normalizing the measured expression level of miR-125b using the measured expression level of the normalizing miR; and c) diagnosing a head and neck cancer in a subject having a normalized measured expression level of miR-125b elevated relative to a reference expression level of miR-125b.

In another aspect, the present disclosure provides a method for assessing the absence or presence of a head and neck cancer in a subject, the method comprising the steps of: a) measuring an expression level of miR-125b in a sample from the subject; b) measuring an expression level of a normalizing miR in the sample and normalizing the measured expression level of miR-125b using the measured expression level of the normalizing miR; and c) assessing the presence of a head and neck cancer in a subject having a normalized measured expression level of miR-125b elevated relative to a reference expression level of miR-125b.

In another aspect, the present disclosure provides a method for identifying a subject who is eligible for a head and neck cancer treatment, the method comprising the steps of: a) measuring an expression level of miR-125b in a sample from the subject; b) measuring an expression level of a normalizing miR in the sample and normalizing the measured expression level of miR-125b using the measured expression level of the normalizing miR; and c) identifying a subject having a normalized measured expression level of miR-125b elevated relative to a reference expression level of miR-125b as eligible for a head and neck cancer treatment.

In another aspect, the present disclosure provides a method for predicting an increase in the likelihood of reoccurrence of a head and neck cancer in a subject, the method comprising the steps of: a) measuring an expression level of miR-125b in a sample from the subject; b) measuring an expression level of a normalizing miR in the sample and normalizing the measured expression level of miR-125b using the measured expression level of the normalizing miR; and c) predicting an increase in the likelihood of a reoccurrence of a head and neck cancer in a subject having a normalized measured expression level of miR-125b elevated relative to a reference expression level of miR-125b.

In another aspect, the present disclosure provides a method comprising treating a subject with an anticancer agent for a head and neck cancer, wherein the subject has a measured expression level of miR-125b in a sample from the subject that is elevated relative to a reference expression level of miR-125b, wherein the measured expression level of miR-125b is normalized using a measured expression level of a normalizing miR in the sample.

In another aspect, the present disclosure provides a method comprising imaging a subject identified as having a head and neck cancer, wherein the subject has a measured expression level of miR-125b in a sample from the subject that is elevated relative to a reference expression level of miR-125b, wherein the measured expression level of miR-125b is normalized using a measured expression level of a normalizing miR in the sample.

The normalized measured expression level of miR-125b may be elevated relative to the reference expression level of miR-125b by at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100%.

In another aspect, the present disclosure provides a method for monitoring a subject undergoing treatment for a head and neck cancer, the method comprising the steps of: a) measuring an expression level of miR-125b in a first sample from the subject at a first period of time; b) measuring an expression level of a normalizing miR in the first sample at the first period of time and normalizing the measured expression level of miR-125b of step a) using the measured expression level of the normalizing miR; c) measuring an expression level of miR-125b in a second sample from the subject at a second period of time; and d) measuring an expression level of a normalizing miR in the second sample at the second period of time and normalizing the measured expression level of miR-125b of step c) using the measured expression level of the normalizing miR, wherein a decrease in the normalized measured expression level of miR-125b in step d) relative to the normalized measured expression level of 125b in step b) is indicative of slowing the progression of a head and neck cancer.

The decrease of the normalized measured expression level of miR-125b in step d) relative to the normalized measured expression level of 125b in step b) indicative of slowing the progression of a head and neck cancer may be a decrease of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100%.

In another aspect, the present disclosure provides a method for predicting an increase in the likelihood of a head and neck cancer developing in a subject, the method comprising the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) predicting an increase in the likelihood of a head and neck cancer developing in a subject having a ratio of normalized measured expression level of miR-342 to normalized measured expression level of miR-125b reduced relative to a reference ratio of expression level of miR-342 to expression level of miR-125b.

In another aspect, the present disclosure provides a method for diagnosing a head and neck cancer in a subject, the method comprising the steps of: a) measuring an expression levels of miR-342 and miR-125b in a sample from the subject; b) measuring an expression level of a normalizing miR in the sample and normalizing the measured expression levels of miR-342 and miR-125b using the measured expression level of the normalizing miR; and c) diagnosing a head and neck cancer in a subject having a ratio of normalized measured expression level of miR-342 to normalized measured expression level of miR-125b reduced relative to a reference ratio of expression level of miR-342 to expression level of miR-125b.

In another aspect, the present disclosure provides a method for assessing the absence or presence of a head and neck cancer in a subject, the method comprising the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) assessing the presence of a head and neck cancer in a subject having a ratio of normalized measured expression level of miR-342 to normalized measured expression level of miR-125b reduced relative to a reference ratio of expression level of miR-342 to expression level of miR-125b.

In another aspect, the present disclosure provides a method for identifying a subject who is eligible for a head and neck cancer treatment, the method comprising the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) identifying a subject having a ratio of normalized measured expression level of miR-342 to normalized measured expression level of miR-125b reduced relative to a reference ratio of expression level of miR-342 to expression level of miR-125b as eligible for a head and neck cancer treatment.

In another aspect, the present disclosure provides a method for predicting an increase in the likelihood of reoccurrence of a head and neck cancer in a subject, the method comprising the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) predicting an increase in the likelihood of a reoccurrence of head and neck cancer in a subject having a ratio of normalized measured expression level of miR-342 to normalized measured expression level of miR-125b reduced relative to a reference ratio of expression level of miR-342 to expression level of miR-125b.

In another aspect, the present disclosure provides a method comprising treating a subject with an anticancer agent for a head and neck cancer, wherein the subject has a ratio of measured expression level of miR-342 to measured expression level of miR-125b in a sample from the subject that is reduced relative to a reference ratio of expression level of miR-342 to expression level of miR-125b, wherein the measured expression level of miR-342 and miR-125b is normalized using a measured expression level of a normalizing miR in the sample.

In another aspect, the present disclosure provides a method comprising imaging a subject identified as having a head and neck cancer, wherein the subject has a ratio of measured expression level of miR-342 to measured expression level of miR-125b in a sample from the subject that is reduced relative to a reference ratio of expression level of miR-342 to expression level of miR-125b, wherein the measured expression level of miR-342 and miR-125b is normalized using a measured expression level of a normalizing miR in the sample.

The ratio of the normalized measured expression level of miR-342 to the normalized measured expression level of miR-125b may be reduced relative to a reference ratio of expression level of miR-342 to expression level of miR-125b by at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, of at least about 60%, of at least about 70%, of at least about 80%, of at least about 90%, or 100%.

The reference ratio of expression level of miR-342 to expression level of miR-125b may be about 36. The reference ratio of expression level of miR-342 to expression level of miR-125b may be about 22.

In another aspect, the present disclosure provides a method for monitoring a subject undergoing treatment for a head and neck cancer, the method comprising the steps of: a) measuring an expression level of miR-342 and miR-125b in a first sample from the subject at a first period of time; b) measuring an expression level of a normalizing miR in the first sample at the first period of time and normalizing the measured expression levels of miR-342 and miR-125b of step a) using the measured expression level of the normalizing miR; c) measuring an expression level of miR-342 and miR-125b in a second sample from the subject at a second period of time; and d) measuring an expression level of a normalizing miR in the second sample at the second period of time and normalizing the measured expression levels of miR-342 and miR-125b of step c) using the measured expression level of the normalizing miR, wherein an elevated ratio of normalized measured expression level of miR-342 to normalized measured expression level of miR-125b in step d) relative to a ratio of normalized measured expression level of miR-342 to normalized measured expression level of 125b in step b) is indicative of slowing the progression of a head and neck cancer.

The decrease of the ratio of the normalized measured expression level of miR-342 to the normalized measured expression level of miR-125b in step d) relative to the ratio of the normalized measured expression level of miR-342 to the normalized measured expression level of 125b in step b) indicative of slowing the progression of a head and neck cancer may be a decrease of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100%.

The normalizing miR may be miR-23b.

Measuring the expression levels may comprise measuring the expression levels with qRT-PCR and normalizing comprises subtracting a Ct value of the measured expression level of miR-342 from a Ct value of the measured expression level of the normalizing miR and/or subtracting a Ct value of the measured expression level of miR-125b from a Ct value of the measured expression level of the normalizing miR.

The sample from the subject may be a body tissue or fluid sample. The body tissue sample may be a bronchial brushing sample. The fluid sample may be a blood sample, a urine sample, a saliva sample, a tear sample, a breast milk sample, a sputum sample, or a semen sample. The fluid sample may be a blood sample.

The head and neck cancer may be a head and neck squamous cell carcinoma (HNSCC). The head and neck cancer may be oral cancer.

In another aspect, the present disclosure provides a use of an miR-125b in a sample from a subject for predicting an increased likelihood of a head and neck cancer developing in the subject.

In another aspect, the present disclosure provides a use of an miR-125b in a sample from a subject for diagnosing a head and neck cancer in the subject.

In another aspect, the present disclosure provides a use of an miR-125b in a sample from a subject for assessing the absence or presence of a head and neck cancer in the subject.

In another aspect, the present disclosure provides a use of an miR-125b in a sample from a subject for identifying the subject's eligibility for a head and neck cancer treatment.

In another aspect, the present disclosure provides a use of an miR-125b in a sample from a subject for predicting an increased likelihood of reoccurrence of a head and neck cancer in the subject.

In another aspect, the present disclosure provides a use of an miR-125b in a sample from a subject for treating a head and neck cancer in the subject.

In another aspect, the present disclosure provides a use of an miR-125b in a sample from a subject for identifying whether the subject is eligible for imaging.

In another aspect, the present disclosure provides a use of an miR-125b in a sample from a subject for monitoring the subject undergoing treatment for a head and neck cancer.

In another aspect, the present disclosure provides a use of an miR-342 and an miR-125b in a sample from a subject for predicting an increased likelihood of a head and neck cancer developing in the subject.

In another aspect, the present disclosure provides a use of an miR-342 and an miR-125b in a sample from a subject for diagnosing a head and neck cancer in the subject.

In another aspect, the present disclosure provides a use of an miR-342 and an miR-125b in a sample from a subject for assessing the absence or presence of a head and neck cancer in the subject.

In another aspect, the present disclosure provides a use of an miR-342 and an miR-125b in a sample from a subject for identifying the subject's eligibility for a head and neck cancer treatment.

In another aspect, the present disclosure provides a use of an miR-342 and an miR-125b in a sample from a subject for predicting an increased likelihood of reoccurrence of a head and neck cancer in the subject.

In another aspect, the present disclosure provides a use of an miR-342 and an miR-125b in a sample from a subject for treating a head and neck cancer in the subject.

In another aspect, the present disclosure provides a use of an miR-342 and an miR-125b in a sample from a subject for identifying whether the subject is eligible for imaging.

In another aspect, the present disclosure provides a use of an miR-342 and an miR-125b in a sample from a subject for monitoring the subject undergoing treatment for a head and neck cancer.

The sample from the subject may be a body tissue or fluid sample. The body tissue sample may be a bronchial brushing sample. The fluid sample may be a blood sample, a urine sample, a saliva sample, a tear sample, a breast milk sample, a sputum sample, or a semen sample. The fluid sample may be a blood sample.

The head and neck cancer may be head and neck squamous cell carcinoma (HNSCC). The head and neck cancer may be oral cancer.

In another aspect, the present disclosure provides a kit for use in predicting an increased likelihood of a head and neck cancer developing in a subject, the kit comprising: a) a probe specific for miR-125b; and b) instructions for use for predicting an increased likelihood of a head and neck cancer developing in the subject.

In another aspect, the present disclosure provides a kit for use in diagnosing a head and neck cancer in a subject, the kit comprising: a) a probe specific for miR-125b; and b) instructions for use for diagnosing a head and neck cancer in the subject.

In another aspect, the present disclosure provides a kit for use in assessing the absence or presence of a head and neck cancer in a subject, the kit comprising: a) a probe specific for miR-125b; and b) instructions for use for assessing the absence or presence of a head and neck cancer in the subject.

In another aspect, the present disclosure provides a kit for use in for identifying a subject eligible for head and neck cancer treatment, the kit comprising: a) a probe specific for miR-125b; and b) instructions for use for identifying a subject eligible for head and neck cancer treatment.

In another aspect, the present disclosure provides a kit for use in predicting an increased likelihood of a reoccurrence of head and neck cancer in a subject, the kit comprising: a) a probe specific for miR-125b; and b) instructions for use for predicting an increased likelihood of a reoccurrence of head and neck cancer.

In another aspect, the present disclosure provides a kit for use in treating a head and neck cancer in a subject, the kit comprising: a) a probe specific for miR-125b; b) an anticancer agent; and c) instructions for use for treating the subject.

In another aspect, the present disclosure provides a kit for use in identifying a subject eligible for imaging, the kit comprising: a) a probe specific for miR-125b; and b) instructions for use for identifying a subject eligible for imaging.

In another aspect, the present disclosure provides a kit for use in monitoring a subject undergoing treatment for a head and neck cancer, the kit comprising: a) a probe specific for miR-125b; and b) instructions for use for monitoring the subject undergoing treatment for a head and neck cancer.

In another aspect, the present disclosure provides a kit for use in predicting an increased likelihood of a head and neck cancer developing in a subject, the kit comprising: a) probe specific for miR-342 and miR-125b; and b) instructions for use for predicting an increased likelihood of a head and neck cancer developing in the subject.

In another aspect, the present disclosure provides a kit for use in diagnosing a head and neck cancer in a subject, the kit comprising: a) probes specific for miR-342 and miR-125b; and b) instructions for use for diagnosing a head and neck cancer in the subject.

In another aspect, the present disclosure provides a kit for use in assessing the absence or presence of a head and neck cancer in a subject, the kit comprising: a) probes specific for miR-342 and miR-125b; and b) instructions for use for assessing the absence or presence of a head and neck cancer in the subject.

In another aspect, the present disclosure provides a kit for use in identifying a subject eligible for head and neck cancer treatment, the kit comprising: a) probes specific for miR-342 and miR-125b; and b) instructions for use for identifying a subject eligible for head and neck cancer treatment.

In another aspect, the present disclosure provides a kit for use in predicting an increased likelihood of a reoccurrence of head and neck cancer in a subject, the kit comprising: a) probes specific for miR-342 and miR-125b; and b) instructions for use for predicting an increased likelihood of a reoccurrence of head and neck cancer.

In another aspect, the present disclosure provides a kit for use in treating a head and neck cancer in a subject, the kit comprising: a) probes specific for miR-342 and miR-125b; b) an anticancer agent; and c) instructions for use for treating the subject.

In another aspect, the present disclosure provides a kit for use in identifying a subject eligible for imaging, the kit comprising: a) probes specific for miR-342 and miR-125b; and b) instructions for use for identifying a subject eligible for imaging.

In another aspect, the present disclosure provides a kit for use in monitoring a subject undergoing treatment for a head and neck cancer, the kit comprising: a) probes specific for miR-342 and miR-125b; and b) instructions for use for monitoring the subject undergoing treatment for a head and neck cancer.

The sample from the subject may be a body tissue or fluid sample. The body tissue sample may be a bronchial brushing sample. The fluid sample may be a blood sample, a urine sample, a saliva sample, a tear sample, a breast milk sample, a sputum sample, or a semen sample. The fluid sample may be a blood sample.

The head and neck cancer may be head and neck squamous cell carcinoma (HNSCC). The head and neck cancer may be oral cancer.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
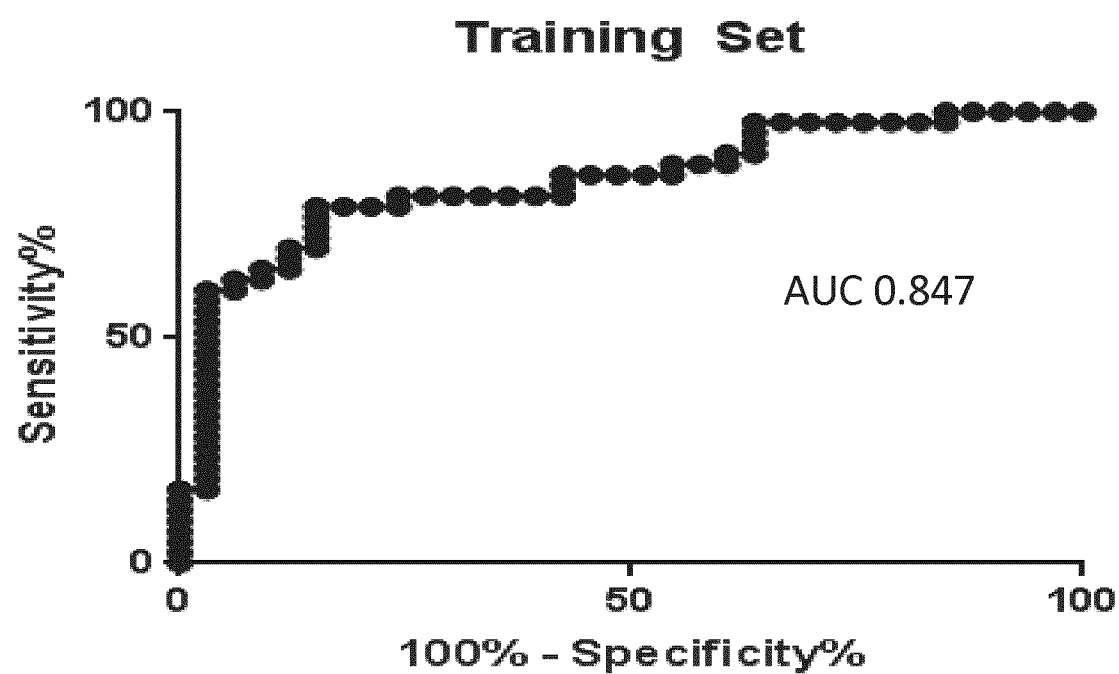
FIG. 1 is a graph illustrating a ROC for a training data set of a classifier according to the present disclosure.

Generally, the present disclosure provides a method for predicting an increase in the likelihood of a head and neck cancer developing in a subject. The method comprises the steps of: a) measuring an expression level of miR-125b in a sample from the subject; b) measuring an expression level of a normalizing miR in the sample and normalizing the measured expression level of miR-125b using the measured expression level of the normalizing miR; and c) predicting an increase in the likelihood of a head and neck cancer developing in a subject having a normalized measured expression level of miR-125b elevated relative to a reference expression level of miR-125b.

The present disclosure also provides a method for diagnosing a head and neck cancer in a subject. The method comprises the steps of: a) measuring an expression level of miR-125b in a sample from the subject; b) measuring an expression level of a normalizing miR in the sample and normalizing the measured expression level of miR-125b using the measured expression level of the normalizing miR; and c) diagnosing a head and neck cancer in a subject having a normalized measured expression level of miR-125b elevated relative to a reference expression level of miR-125b.

The present disclosure also provides a method for assessing the absence or presence of a head and neck cancer in a subject. The method comprises the steps of: a) measuring an expression level of miR-125b in a sample from the subject; b) measuring an expression level of a normalizing miR in the sample and normalizing the measured expression level of miR-125b using the measured expression level of the normalizing miR; and c) assessing the presence of a head and neck cancer in a subject having a normalized measured expression level of miR-125b elevated relative to a reference expression level of miR-125b.

The present disclosure also provides a method for identifying a subject who is eligible for a head and neck cancer treatment. The method comprises the steps of: a) measuring an expression level of miR-125b in a sample from the subject; b) measuring an expression level of a normalizing miR in the sample and normalizing the measured expression level of miR-125b using the measured expression level of the normalizing miR; and c) identifying a subject having a normalized measured expression level of miR-125b elevated relative to a reference expression level of miR-125b as eligible for a head and neck cancer treatment.

The present disclosure also provides a method for predicting an increase in the likelihood of reoccurrence of a head and neck cancer in a subject. The method comprises the steps of: a) measuring an expression level of miR-125b in a sample from the subject; b) measuring an expression level of a normalizing miR in the sample and normalizing the measured expression level of miR-125b using the measured expression level of the normalizing miR; and c) predicting an increase in the likelihood of a reoccurrence of a head and neck cancer in a subject having a normalized measured expression level of miR-125b elevated relative to a reference expression level of miR-125b.

The present disclosure also provides a method comprising treating a subject with an anticancer agent for a head and neck cancer, wherein the subject has a measured expression level of miR-125b in a sample from the subject that is elevated relative to a reference expression level of miR-125b, wherein the measured expression level of miR-125b is normalized using a measured expression level of a normalizing miR in the sample.

The present disclosure also provides a method comprising imaging a subject identified as having a head and neck cancer, wherein the subject has a measured expression level of miR-125b in a sample from the subject that is elevated relative to a reference expression level of miR-125b, wherein the measured expression level of miR-125b is normalized using a measured expression level of a normalizing miR in the sample.

The present disclosure also provides a method for monitoring a subject undergoing treatment for a head and neck cancer. The method comprises the steps of: a) measuring an expression level of miR-125b in a first sample from the subject at a first period of time; b) measuring an expression level of a normalizing miR in the first sample at the first period of time and normalizing the measured expression level of miR-125b of step a) using the measured expression level of the normalizing miR; c) measuring an expression level of miR-125b in a second sample from the subject at a second period of time; and d) measuring an expression level of a normalizing miR in the second sample at the second period of time and normalizing the measured expression level of miR-125b of step c) using the measured expression level of the normalizing miR, wherein a decrease in the normalized measured expression level of miR-125b in step d) relative to the normalized measured expression level of 125b in step b) is indicative of slowing the progression of a head and neck cancer.

The present disclosure also provides a method for predicting an increase in the likelihood of a head and neck cancer developing in a subject. The method comprises the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) predicting an increase in the likelihood of a head and neck cancer developing in a subject having a ratio of normalized measured expression level of miR-342 to normalized measured expression level of miR-125b reduced relative to a reference ratio of expression level of miR-342 to expression level of miR-125b.

The present disclosure also provides a method for diagnosing a head and neck cancer in a subject. The method comprises the steps of: a) measuring an expression levels of miR-342 and miR-125b in a sample from the subject; b) measuring an expression level of a normalizing miR in the sample and normalizing the measured expression levels of miR-342 and miR-125b using the measured expression level of the normalizing miR; and c) diagnosing a head and neck cancer in a subject having a ratio of normalized measured expression level of miR-342 to normalized measured expression level of miR-125b reduced relative to a reference ratio of expression level of miR-342 to expression level of miR-125b.

The present disclosure also provides a method for assessing the absence or presence of a head and neck cancer in a subject. The method comprises the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) assessing the presence of a head and neck cancer in a subject having a ratio of normalized measured expression level of miR-342 to normalized measured expression level of miR-125b reduced relative to a reference ratio of expression level of miR-342 to expression level of miR-125b.

The present disclosure also provides a method for identifying a subject who is eligible for a head and neck cancer treatment. The method comprises the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) identifying a subject having a ratio of normalized measured expression level of miR-342 to normalized measured expression level of miR-125b reduced relative to a reference ratio of expression level of miR-342 to expression level of miR-125b as eligible for a head and neck cancer treatment.

The present disclosure also provides a method for predicting an increase in the likelihood of reoccurrence of a head and neck cancer in a subject. The method comprises the steps of: a) measuring an expression level of miR-342 and miR-125b in a sample from the subject; b) measuring an expression level of a normalizing miR in the sample and normalizing the measured expression levels of miR-342 and miR-125b using the measured expression level of the normalizing miR; and c) predicting an increase in the likelihood of a reoccurrence of head and neck cancer in a subject having a ratio of normalized measured expression level of miR-342 to normalized measured expression level of miR-125b reduced relative to a reference ratio of expression level of miR-342 to expression level of miR-125b.

The present disclosure also provides a method comprising treating a subject with an anticancer agent for a head and neck cancer, wherein the subject has a ratio of measured expression level of miR-342 to measured expression level of miR-125b in a sample from the subject that is reduced relative to a reference ratio of expression level of miR-342 to expression level of miR-125b, wherein the measured expression level of miR-342 and miR-125b is normalized using a measured expression level of a normalizing miR in the sample.

The present disclosure also provides a method comprising imaging a subject identified as having a head and neck cancer, wherein the subject has a ratio of measured expression level of miR-342 to measured expression level of miR-125b in a sample from the subject that is reduced relative to a reference ratio of expression level of miR-342 to expression level of miR-125b, wherein the measured expression level of miR-342 and miR-125b is normalized using a measured expression level of a normalizing miR in the sample.

The present disclosure also provides a method for monitoring a subject undergoing treatment for a head and neck cancer. The method comprises the steps of: a) measuring an expression level of miR-342 and miR-125b in a first sample from the subject at a first period of time; b) measuring an expression level of a normalizing miR in the first sample at the first period of time and normalizing the measured expression levels of miR-342 and miR-125b of step a) using the measured expression level of the normalizing miR; c) measuring an expression level of miR-342 and miR-125b in a second sample from the subject at a second period of time; and d) measuring an expression level of a normalizing miR in the second sample at the second period of time and normalizing the measured expression levels of miR-342 and miR-125b of step c) using the measured expression level of the normalizing miR, wherein an elevated ratio of normalized measured expression level of miR-342 to normalized measured expression level of miR-125b in step d) relative to a ratio of normalized measured expression level of miR-342 to normalized measured expression level of 125b in step b) is indicative of slowing the progression of a head and neck cancer.

The present disclosure also provides uses and kits associated with the herein disclosed methods. The present disclosure provides a use of an anticancer agent for treating a head and neck cancer in a subject, wherein the subject has a measured expression level of miR-125b in a sample from the subject that is elevated relative to a reference expression level of miR-125b, wherein the measured expression level of miR-125b is normalized using a measured expression level of a normalizing miR in the sample. The present disclosure also provides a use of an anticancer agent for treating a head and neck cancer in a subject, wherein the subject has a ratio of measured expression level of miR-342 to measured expression level of miR-125b in a sample from the subject that is reduced relative to a reference ratio of expression level of miR-342 to expression level of miR-125b, wherein the measured expression level of miR-342 and miR-125b is normalized using a measured expression level of a normalizing miR in the sample.

In the context of the present disclosure, head and neck cancer refers to any cancer that starts in the mouth, nose, pharynx, larynx, sinuses, or salivary glands. Examples of head and neck cancers include: head and neck squamous cell carcinoma (HNSCC), oral cancer, cancer of the oral cavity, mouth cancer, cancer of the nasal cavity, nasopharyngeal cancer, cancer of the sinuses, throat cancer, pharyngeal cancer, cancer of the pharynx, cancer of the larynx, laryngeal cancer, nasopharyngeal cancer, cancer of the salivary gland, cancer of the tonsils.

The authors of the present disclosure have developed methods that use a microRNA (miRNA) signature comprising miR-125b or miR-125b and miR-342 that may: (1) predict, detect and/or analyze an initial occurrence of head and neck cancer in a subject at an earlier disease stage than one or more known methods that do not use miR-125b or miR-125b and miR-342; (2) predict, detect, and/or analyze a reoccurrence of head and neck cancer in a subject at an earlier disease stage than one or more known methods that do not use miR-125b or miR-125b and miR-342; (3) decrease the invasiveness of predicting, detecting, and/or analyzing head and neck cancer compared to the one or more known methods that do not use miR-125b or miR-125b and miR-342; (4) predict, detect, and/or analyze head and neck cancer more accurately than one or more known methods that do not use miR-125b or miR-125b and miR-342; or (5) a combination thereof.

A miRNA refers to an endogenous non-coding RNA oligonucleotide that acts as a post-transcriptional regulator of gene expression in multicellular organisms. As used herein, the term "oligonucleotide" refers to a polymeric form of nucleotides of any length, either deoxyribonucleotides or ribonucleotides, or analogs thereof. In the context of the present disclosure, a miRNA refers to a mature miRNA molecule, also termed "miR", or a precursor thereof, which is a hairpin structure comprising 60-120 nucleotides and cleaved from a pri-miRNA in the nucleus by a double-strand-specific ribonuclease.

A miRNA signature refers to one or more miRNAs that are associated with a specific trait. In some examples according to the present disclosure, the miRNA signature comprises miR-125b or miR-125b and miR-342. In other examples according to the present disclosure, the miRNA signature consists of miR-125b or miR-125b and miR-342. The herein described miRNAs in a miRNA signature may be referred to as a "biomarker".

miRNA-342 and miR-125b follow the standardized criteria and conventions for miRNA identification and naming, which are outlined on miRBase (http://www.mirbase.org/help/nomencature.shtml) and described in the article: Victor Ambros, Bonnie Bartel, David P. Bartel, Christopher B. Burge, James C. Carrington, Xuemei Chen, Gideon Dreyfuss, Sean R. Eddy, Sam Griffiths-Jones, Mhair Marshall, Marjo Matzke, Gary Ruvkun, and Thomas Tuschl. A uniform system for microRNA annotation. RNA 2003 9(3): 277-279.

The miR-342 may comprise an oligonucleotide having the sequence: AGGGGUGCUAUCUGUGAUUGA (SEQ ID NO:1) or UCUCACACAGAAAUCGCACCCGU (SEQ ID NO:2), or may comprise an oligonucleotide having a sequence that has at least about 85%, about 90%, about 95%, or about 99% sequence identity to SEQ ID NO:1 or SEQ ID NO:2. In some examples according to the present disclosure, the miR-342 consists of an oligonucleotide having the sequence identified as SEQ ID NO:1 or SEQ ID NO:2, or consists of an oligonucleotide having a sequence that has at least about 85%, about 90%, about 95%, or about 99% sequence identity to SEQ ID NO:1 or SEQ ID NO:2. In some examples according to the present disclosure, the miR-342 is identified as "hsa-miR-342-5p MIMAT0004694" or "hsa-miR-342-3p MIMAT0000753".

The precursor of miR-342 may comprise an oligonucleotide having the sequence:

```
                                        (SEQ ID NO: 3)
GAAACUGGGCUCAAGGUGAGGGGUGCUAUCUGUGAUUGAGGGACAUGGUU

AAUGGAAUUGUCUCACACAGAAAUCGCACCCGUCACCUUGGCCUACUUA,
``` or may comprise an oligonucleotide having a sequence that has at least about 85%, about 90%, about 95%, or about 99% sequence identity to SEQ ID NO:3. In some examples according to the present disclosure, the precursor of miR-342 consists of an oligonucleotide having the sequence identified as SEQ ID NO:3, or consists of an oligonucleotide having a sequence that has at least about 85%, about 90%, about 95%, or about 99% sequence identity to SEQ ID NO:3. In some examples according to the present disclosure, the precursor of miR-342 is identified as "hsa-mir-342 M10000805".

The miR-125b may comprise an oligonucleotide having the sequence: UCCCUGAGACCCUAACUUGUGA (SEQ ID NO:4), or may comprise an oligonucleotide having a sequence that has at least about 85%, about 90%, about 95%, or about 99% sequence identity to SEQ ID NO:4. In some examples according to the present disclosure, the miR-125b consists of an oligonucleotide having the sequence identified as SEQ ID NO:4, or consists of an oligonucleotide having a sequence that has at least about 85%, about 90%, about 95%, or about 99% sequence identity to SEQ ID NO:4. In some examples according to the present disclosure, the miR-125b is identified as "hsa-miR-125b-5p MIMAT0000423".

The precursor of miR-125b may comprise an oligonucleotide having the sequence: UGCGCUCCUCUCAGUCC-CUGAGACCCUAACUUGUGAU-GUUUACCGUUUAAAUCCA CGGGUUAGGCUCUUGGGAGCUGCGAGUCGUGCU (SEQ ID NO:5), or may comprise an oligonucleotide having a sequence that has at least about 85%, about 90%, about 95%, or about 99% sequence identity to SEQ ID NO:5. In some examples according to the present disclosure, the precursor of miR-125b consists of an oligonucleotide having the sequence identified as SEQ ID NO:5, or consists of an oligonucleotide having a sequence that has at least about 85%, about 90%, about 95%, or about 99% sequence identity to SEQ ID NO:5. In some examples according to the present disclosure, the precursor of miR-125b is identified as "hsa-mir-125b-1 M10000446".

The percentage of sequence identity for oligonucleotides is calculated by aligning the sequences being compared, and then counting the number of shared residues at each aligned position. No penalty is imposed for the presence of insertions or deletions, but are permitted only where required to accommodate an obviously increased number of nucleotide residues in one of the sequences being aligned. When one of the sequences being compared is indicated as being "contiguous", then no gaps are permitted in that sequence during the comparison. The percentage identity is given in terms of residues in the test sequence that are identical to residues in the comparison or reference sequence.

Measuring the expression levels of miRNA refers to any technique that is able to determine the amount of miRNA in a sample. Examples of techniques that may be used to measure the expression levels of miRNA in a sample include real-time Polymerase Chain Reaction (qPCR), microarray, nanostring, RNA sequencing, northern blot, and in situ hybridization. In some examples according to the present disclosure, qPCR is used for measuring the expression levels of miRNA, for example when: (1) decreasing the cost of performing the method, which may be a result of laboratories already having the necessary equipment and skillset to perform qPCR; (2) decreasing the overall time scale for measuring expression levels of miRNA; or (3) a combination therefore, is preferable. In some examples according to the present disclosure, microarray or nanostring is used for measuring the expression levels of miRNA, for example when increasing the quantitativeness of measurement is preferable.

The sample may be any tissue or fluid obtained from a subject. In the context of the present disclosure, the subject may be any animal. Preferably, the subject is a human being. The tissue sample may be a tissue biopsy, a tumor biopsy, a cancer tissue, or a combination thereof. The tissue sample may be: (1) present or start in the mouth, nose, pharynx, larynx, sinuses, or salivary glands, for example, squamous epithelial cells; (2) present or start in a tumor; or (3) a combination thereof. The tissue sample may be obtained from a subject that: (1) is not showing one or more signs or symptoms associated with a head and neck cancer or is showing one or more signs or symptoms associated with a head and neck cancer; (2) has not been identified as having a head and neck cancer or has been identified as having a head and neck cancer, for example, the tumor sample may be a sample from a head and neck cancer tumor; (3) has not been previously identified as having a head and neck cancer or has been previously identified as having a head and neck cancer; or (4) a combination thereof. The fluid sample may be a blood sample, a urine sample, a saliva sample, a tear sample, a breast milk sample, a sputum sample, a feces sample, a semen sample, a cerebrospinal fluid sample, a sweat sample, a lacrimol secretion sample, a lymph sample, or a nasal mucosa sample. The fluid sample may be obtained from a subject that: (1) is not showing one or more signs or symptoms associated with a head and neck cancer or is showing one or more signs or symptoms associated with a head and neck cancer; (2) has not been identified as having a head and neck cancer or has been identified as having a head and neck cancer (3) has not been previously identified as having a head and neck cancer or has been previously identified as having a head and neck cancer; or (4) a combination thereof. In some examples according to the present disclosure, the sample is a fluid sample, for example when: (1) obtaining a sample from a subject less invasively as compared to one or more known methods for evaluating head and neck cancers; (2) obtaining a sample from a subject over a shorter time period as compared to one or more known methods for evaluating head and neck cancers; (3) obtaining a larger number of samples from a subject as compared to one or more known methods for evaluating head and neck cancers; (4) decreasing the disturbance with a subject's body in an area that may be the location of a tumor and require further assessment as compared to one or more known methods for evaluating head and neck cancers; (5) obtaining a sample from a subject where the location of a tumor is unknown; or (6) a combination thereof, is preferable. In some examples according to the present disclosure, the fluid sample is a serum sample, for example when: (1) decreasing the cost of the sampling, which may be a result of laboratories already having the equipment and skillset to perform blood sampling; (2) decreasing the overall time scale of the sampling; or (3) a combination therefore, is preferable.

Obtaining a sample from a subject refers to any technique that is able to extract a sufficient amount of tissue or fluid sample from the subject to measure the expression level of miRNA in the sample. Examples of techniques for obtaining a sample include venipuncture, biopsy, and bronchial brushing, bronchial biopsy, buccal brushing, buccal biopsy, cytological brushing, cytological biopsy, exhaled breath, and a mucosal swab. In herein disclosed methods that include obtaining more than one sample from a subject, it is preferable that the sample type and the technique for obtaining the samples is the same across the more than one sample.

Normalizing the measured expression levels of miRNA refers to any technique that is able to decrease systematic technical or experimental variations during measurement, for example, by correcting measured expression levels of miRNAs of interest against one or more endogenous reference miRNAs. A skilled person would understand that the type of normalizing technique utilized may depend on the type of measuring technique employed as well as the sample type, for example, serum analysis of the expression of a miRNA may not be the same as the expression of the miRNA in the cell. Examples of normalizing measured expression levels of miRNA include using an internal control, global mean normalization, algorithmic correction that is devised based on large samples, or a combination thereof. U6 may be used as an internal control, for example when evaluating gene expression in cells because it is believed to be expressed at the same level in all cells all the time. When evaluating a larger set of genes or miRNAs, for example when using a microarray, global mean normalization may be used. Preferably, algorithmic correction is used, for example when normalizing the measured expression levels of one or two miRNAs.

In some examples according to the present disclosure, qPCR is used to measure the expression levels of miRNA. To increase the reliability of the comparison of miRNA expression levels in qPCR, normalization may be used to correct for intra- and intergroup variations in between samples and runs. A preferable miRNA normalization standard in qPCR expression profiling may provide: (1) about equal transcription level in all tissues and cell types at all stages of development; (2) about stable transcription levels during external or internal stimulation; or (3) a combination thereof. In the context of the present disclosure, the miRNA normalization standard is also referred to as a normalizing miR. Any normalizing miR that shows decreased variability between normal and cancer samples may be used with the herein disclosed methods. As described in more detail in the examples section, the authors of the present disclosure utilized different algorithms to analyze the data consisting of expression for 742 miRNAs in over 100 samples in both cancer and control. The algorithmic correction selected the herein used normalizing miRNAs that showed the least amount of variability and that were present in every sample. In some examples according to the present disclosure, the normalizing miR is hsa-miR-23b, hsa-miR-7e, hsa-miR-145, or a combination thereof. Preferably, the normalizing miR is hsa-miR-23b, which in the context of the present disclosure, showed the least variability between the normal and cancer samples.

The authors of the present disclosure have determined that an expression level of miR-125b or a ratio of miR-342 expression level to miR-125b expression level, can be used to: (1) predict an increase in the likelihood of a head and neck cancer developing in a subject; (2) diagnose a head and neck cancer in a subject; (3) assess the absence or presence of a head and neck cancer in a subject; (4) identify a subject who is eligible for a head and neck cancer treatment; (5) predict an increase in the likelihood of reoccurrence of a head and neck cancer in a subject; (6) treat a subject with an anticancer agent for a head and neck cancer; (7) image a subject identified as having a head and neck cancer; (8) monitor a subject undergoing treatment for a head and neck cancer or (9) a combination thereof, at: (1) an increased accuracy; (2) an earlier disease stage; (3) a decreased invasiveness; or (4) a combination thereof, compared to one or more known head and neck detection methods that do not use miR-125b or miR-342 and miR-125b. Importantly, the authors determined that the expression level of miR-342 alone could not be used to: (1) predict an increase in the likelihood of a head and neck cancer developing in a subject; (2) diagnose a head and neck cancer in a subject; (3) assess the absence or presence of a head and neck cancer in a subject; (4) identify a subject who is eligible for a head and neck cancer treatment; (5) predict an increase in the likelihood of reoccurrence of a head and neck cancer in a subject;

(6) treat a subject with an anticancer agent for a head and neck cancer; (7) image a subject identified as having a head and neck cancer; (8) monitor a subject undergoing treatment for a head and neck cancer; or (9) a combination thereof, at a sufficient accuracy for clinical utility. A sufficient accuracy for clinical utility may vary depending on a balance of a desire for detection at an early disease stage with tolerance for false positives and negatives. In some examples according to the present disclosure, a sufficient accuracy for clinical utility is an AUC value of about 0.8 or higher.

The authors of the present disclosure determined that when an expression level of miR-125b is elevated relative to a reference expression level of miR-125b, the subject may be: (1) predicted to have an increase in the likelihood of developing a head and neck cancer (2) diagnosed with a head and neck cancer; (3) assessed for the absence or presence of a head and neck cancer; (4) identified as eligible for a head and neck cancer treatment; (5) predicted to have an increase in the likelihood of reoccurrence of a head and neck cancer; (6) treated with an anticancer agent; (7) imaged; or (8) a combination thereof, at: (1) an increased accuracy; (2) an earlier disease stage; (3) a decreased invasiveness; or (4) a combination thereof, compared to one or more known head and neck detection methods that do not use miR-125b.

An elevation of the expression level of miR-125b relative to a reference expression level of miR-125b may be an elevation of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100%.

The authors of the present disclosure also determined that when the ratio of an expression level of miR-342 to an expression level of miR-125b in a subject is reduced relative to a reference ratio of expression level of miR-342 to expression level of miR-125b, the subject may be: (1) predicted to have an increase in the likelihood of developing a head and neck cancer; (2) diagnosed with a head and neck cancer; (3) assessed for the absence or presence of a head and neck cancer; (4) identified as eligible for a head and neck cancer treatment; (5) predicted to have an increase in the likelihood of reoccurrence of a head and neck cancer; (6) treated with an anticancer agent; (7) imaged; or (8) a combination thereof, at: (1) an increased accuracy; (2) an earlier disease stage; (3) a decreased invasiveness; or (4) a combination thereof, compared to one or more known head and neck detection methods that do not use miR-342 and miR-125b.

A reduction in the ratio of an expression level of miR-342 to an expression level of miR-125b relative to a reference ratio of expression level of miR-342 to expression level of miR-125b may be a reduction of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100%.

In some examples according to the present disclosure, the reference ratio of the expression level of miR-342 to the expression level of miR-125b may be about 36 or higher. Accordingly, when a ratio of the expression level of miR-342 to the expression level of miR-125b in a subject is reduced to about 36 or less, the subject may be: (1) predicted to have an increase in the likelihood of developing a head and neck cancer; (2) diagnosed with a head and neck cancer (3) assessed for the absence or presence of a head and neck cancer; (4) identified as eligible for a head and neck cancer treatment; (5) predicted to have an increase in the likelihood of reoccurrence of a head and neck cancer (6) treated with an anticancer agent; (7) imaged; or (8) a combination thereof. In some examples according to the present disclosure, the reference ratio of the expression level of miR-342 to the expression level of miR-125b may be about 22 or higher.

The reference expression level of miR-125b or the reference ratio of expression level of miR-342 to expression level of miR-125b may be from a control subject that does not have a head and neck cancer. Preferably, the expression level of miR-125b or the ratio of expression levels of miR-342 and miR-125b of the subject and the control subject are measured in a corresponding or similar sample type. In some examples according to the present disclosure, the control subject is demographically-matched to the subject, for example by age, sex, smoking status, drinking habits, or a combination thereof. The reference expression level or the reference ratio from the control subject may be measured at the time of measuring the subject, or the reference expression level or reference ratio may have been previously measured and stored in a database.

The authors of the present disclosure also determined that monitoring the expression level of miR-125b in a subject over time may be used to monitor the subject while the subject is undergoing treatment for a head and neck cancer. A measured expression level that is decreased from a first time period to a second time period following the first time period is indicative of the slowing of the progression of the head and neck cancer. In some examples according to the present disclosure, the decreased expression level of miR-125b indicative of slowing of the progression of the head and neck cancer in a subject is a decrease of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100% from the first time period to the second time period.

The authors of the present disclosure also determined that monitoring the ratio of expression level of miR-342 to expression level of miR-125b in a subject over time may be used to monitor the subject while the subject is undergoing treatment for a head and neck cancer. A ratio that is elevated from a first time period to a second time period following the first time period is indicative of the slowing of the progression of the head and neck cancer. In some examples according to the present disclosure, the elevated ratio of expression level of miR-342 to expression level of miR-125b indicative of slowing of the progression of the head and neck cancer in a subject is an elevation of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100% from the first time period to the second time period.

Figure 6:
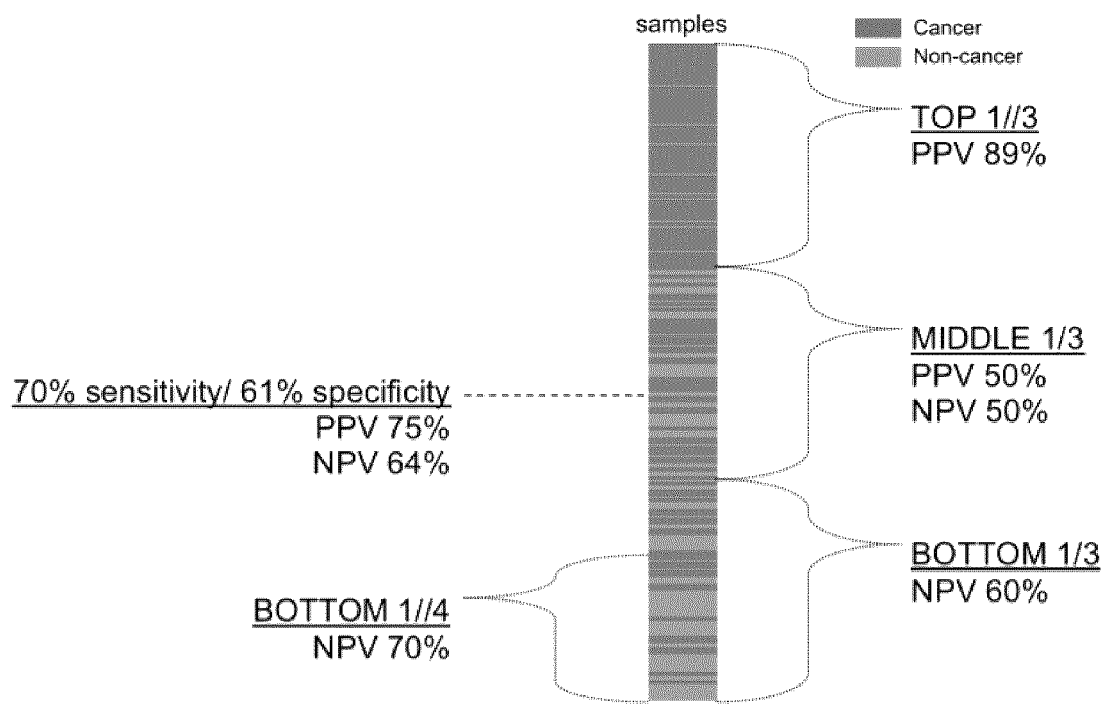
FIG. 6 is an illustration showing biomarker threshold values. Equation values for each sample were ordered. Red/dark indicates a cancer sample and blue/light a non-cancer control sample. PPV (positive predictive value) NPV (negative predictive value).

Threshold cutoffs may be used to: (1) predict an increase in the likelihood of a head and neck cancer developing in a subject; (2) diagnose a head and neck cancer in a subject; (3) assess the absence or presence of a head and neck cancer in a subject; (4) identify a subject who is eligible for a head and neck cancer treatment; (5) predict an increase in the likelihood of reoccurrence of a head and neck cancer in a subject; (6) treat a subject with an anticancer agent for a head and neck cancer; (7) image a subject identified as having a head and neck cancer; (8) monitor a subject undergoing treatment for a head and neck cancer; or (9) a combination thereof, at: (1) an increased accuracy; (2) an earlier disease stage; (3) a decreased invasiveness; or (4) a combination thereof, compared to one or more known head and neck detection methods that do not use miR-125b or miR-342 and miR-125b. Threshold cutoffs may be pre-determined, for example when the clinical utility of the herein described biomarkers are being assessed with a single sample run. The threshold selected may be used to define the sensitivity and specificity of the test. To select the desirable threshold, the application of the test may be the main consideration. For example, if one were to use a test for brain cancer where the outcome of the test would result in brain surgery, the test may require high sensitivity and specificity since the cost for brain surgery would be insufficiently high if the test was incorrect. However, if the outcome of a test had a less invasive outcome, for example, a biopsy or imaging, then the sensitivity and specificity may be relaxed. A test can have several thresholds that result in different sensitivities and specificities. For example, in FIG. 6, the authors show how the data for their test classifies the group of control samples and cancer samples. If the user of the test wished to increase their certainty that a positive test indicates the presence of disease, a more stringent cutoff at the top ⅓ of the cases may be preferable. However, this may result in more individuals with cancer going undetected by the biomarker. If the clinician felt that having a few false positives resulting in unnecessary imaging for these patients is acceptable in order to aid in the early diagnosis for more people, then a less stringent threshold may be preferable.

Predicting an increase in the likelihood of a head and neck cancer refers to recognizing that a subject that is not showing one or more signs or symptoms associated with a head and neck cancer is more susceptible to developing a head and neck cancer compared to a control group of control subjects. Predicting an increase in the likelihood of reoccurrence of a head and neck cancer in a subject refers to recognizing that a subject is more susceptible to reoccurrence of a head and neck cancer compared to a control group of control subjects. Examples of signs and symptoms that are associated with head and neck cancer would be understood by a person skilled in the art; examples of which are: a lump in the nose, neck or throat, with or without pain; a persistent sore throat; trouble swallowing (e.g. dysphagia); unexplained weight loss; frequent coughing; change in voice or hoarseness; ear pain or trouble hearing; headaches; a red or white patch in the mouth; bad breath that is unexplained by hygiene; nasal obstruction or persistent congestion; frequent nose bleeds or unusual discharge; and trouble breathing.

The herein disclosed methods for predicting an increase in the likelihood of a subject developing a head and neck cancer or for predicting an increase in the likelihood of reoccurrence of a head and neck cancer in a subject may be performed at any time the subject is not showing one or more signs or symptoms associated with head and neck cancer, for example, during a periodic screening or during a standard follow up. In some examples according to the present disclosure, the herein disclosed methods for predicting an increase in the likelihood of a subject developing head and neck cancer or for predicting an increase in the likelihood of reoccurrence of a head and neck cancer in a subject is used as a screen on a high risk subject, for example, a heavy smoker, a heavy drinker, a subject exposed to HPV, a subject with a compromised immune system, or a combination thereof. In some examples according to the present disclosure, the herein disclosed methods for predicting an increase in the likelihood of a subject developing head and neck cancer or for predicting an increase in the likelihood of reoccurrence of a head and neck cancer in a subject is used during standard follow up when the subject's previous bout with head and neck cancer is in remission.

The herein disclosed methods for predicting an increase in the likelihood of a subject developing a head and neck cancer or for predicting an increase in the likelihood of reoccurrence of a head and neck cancer in a subject may be performed from about 1 to about 365 days earlier than one or more known methods for predicting an increase in the likelihood of developing a head and neck cancer and/or for predicting an increase in the likelihood of reoccurrence of a head and neck cancer that do not use miR-125b or miR-342 and miR-125b.

The herein disclosed methods for predicting an increase in the likelihood of a subject developing head and neck cancer or for predicting an increase in the likelihood of reoccurrence of a head and neck cancer in a subject may be performed at periodic time points, for example, each day, each week, every two weeks, every three weeks, every four weeks, each month, every two months, every three months, every four months, every five months, every six months, or every year that the subject is not showing one or more signs or symptoms associated with a head and neck cancer.

A subject may be identified as having an increased likelihood of developing head and neck cancer or an increased likelihood of reoccurrence of a head and neck cancer when an expression level of miR-125b in the subject is elevated relative to a reference expression level of miR-125b, or when the ratio of expression level of miR-342 to expression level of miR-125b in the subject is reduced relative to a reference ratio of expression level of miR-342 to expression level of miR-125b at at least 1 time point, at least 2 time points, at least 3 time points, at least 4 time points, at least 5 time points, at least 6 time points, at least 7 time points, at least 8 time points, at least 9 time points, or at least 10 time points.

Diagnosing head and neck cancer refers to identifying a head and neck cancer in a subject that is showing one or more signs or symptoms associated with a head and neck cancer. Diagnosing head and neck cancer may include: (1) identifying an initial head and neck cancer in a subject that has not previously been diagnosed with a head and neck cancer; (2) identifying a reoccurrence of a head and neck cancer in a subject that has previously been diagnosed with the same or a different head and neck cancer or (3) a combination thereof. Signs and symptoms that may be associated with head and neck cancer refers to: (1) signs and symptoms that are known to be associated with a specified type of head and neck cancer; (2) signs and symptoms that are non-specific to a type of head and neck cancer; or (3) a combination thereof.

The herein described methods for diagnosing a head and neck cancer may be performed at any time that the subject shows one or more signs or symptoms associated with head and neck cancer. In some examples according to the present disclosure, the herein disclosed methods for diagnosing head and neck cancer may be performed from about 1 to about 365 days earlier than one or more known methods for diagnosing head and neck cancer that do not use miR-125b or miR-342 and miR-125b. The known standard for follow up after treatment for a head and neck cancer is a clinical exam. Scar tissue from primary head and neck cancer treatment may make it difficult to determine if tumor tissue remains following treatment because everything feels like a lump, which may result in the recurrent disease not being diagnosed until additional signs or symptoms are detected. The herein disclosed methods are not reliant on tumor location for diagnosing head and neck cancer and therefore may be utilized to diagnose head and neck cancer earlier than one or more known standard clinical examinations.

The herein disclosed methods for diagnosing head and neck cancer may be performed at periodic time points, for example, each day, each week, every two weeks, every three weeks, every four weeks, each month, every two months, every three months, every four months, every five months, every six months, and/or every year that the subject is showing one or more signs or symptoms associated with a head and neck cancer.

A subject may be diagnosed with a head and neck cancer when an expression level of miR-125b in the subject is elevated relative to a reference expression level of miR-125b, or when the ratio of expression level of miR-342 to expression level of miR-125b in the subject is reduced relative to a reference ratio of expression level of miR-342 to expression level of miR-125b at at least 1 time point, at least 2 time points, at least 3 time points, at least 4 time points, at least 5 time points, at least 6 time points, at least 7 time points, at least 8 time points, at least 9 time points, or at least 10 time points.

Assessing the absence or presence of a head and neck cancer refers to identifying a head and neck cancer in a subject that may or may not be showing one or more signs or symptoms that is associated with a head and neck cancer.

The expression levels of miR-125b or miR-342 and miR-125b may be measured at any time. In some examples according to the present disclosure, the herein disclosed methods for assessing the absence or presence of a head and neck cancer may be performed from about 1 to about 365 days earlier than one or more known methods for diagnosing head and neck cancer that do not use miR-125b or miR-342 and miR-125b.

The herein disclosed methods for assessing the absence or presence of head and neck cancer may be performed at periodic time points, for example, each day, each week, every two weeks, every three weeks, every four weeks, each month, every two months, every three months, every four months, every five months, every six months, and/or every year.

A subject may be assessed for the presence of a head and neck cancer when an expression level of miR-125b in the subject is elevated relative to a reference expression level of miR-125b or when the ratio of expression level of miR-342 to expression level of miR-125b in the subject is reduced relative to a reference ratio of expression level of miR-342 to expression level of miR-125b at at least 1 time point, at least 2 time points, at least 3 time points, at least 4 time points, at least 5 time points, at least 6 time points, at least 7 time points, at least 8 time points, at least 9 time points, or at least 10 time points.

Identifying a subject who is eligible for a head and neck cancer treatment refers to recognizing that a subject is suitable for one or more head and neck cancer treatments. Examples of head and neck cancer treatments include: performing surgery, performing radiation therapy, performing chemotherapy, performing targeted therapy, performing immune therapy, administering an anticancer agent, or a combination thereof. Examples of anticancer agents for treating head and neck cancer include cisplatin, carboplatin, fluorouracil, cetuximab, docetaxel, leucovorin, methotrexate, nivolumab, paclitaxel, etoposide, and pembrolizumab.

The herein described methods for identifying a subject who is eligible for a head and neck cancer treatment may be performed at any time the subject shows one or more signs or symptoms associated with head and neck cancer. In some examples according to the present disclosure, the herein disclosed methods for identifying a subject who is eligible for a head and neck cancer treatment may be performed from about 1 to about 365 days earlier than one or more known methods for diagnosing head and neck cancer that do not use miR-125b or miR-342 and miR-125b. An earlier assessment of the eligibility of a subject for head and neck cancer treatment compared to one or more known methods may allow for an assessment at an earlier stage of the disease, which may increase the availability of options for treatment. For example, in a case where a tumor cannot be imaged, surgery and radiation may not be a desirable treatment option. An earlier identification of a subject as being eligible for a head and neck cancer using the herein disclosed methods may allow for alternative treatment options that do not require the location of the tumor, for example, chemotherapy or immune therapy.

The herein disclosed methods for identifying a subject who is eligible for a head and neck cancer treatment may be performed at periodic time points, for example, each day, each week, every two weeks, every three weeks, every four weeks, each month, every two months, every three months, every four months, every five months, every six months, and/or every year that the subject shows one or more signs or symptoms associated with head and neck cancer.

A subject may be identified as eligible for a head and neck cancer treatment when an expression level of miR-125b in the subject is elevated relative to a reference expression level of miR-125b, or when the ratio of expression level of miR-342 to expression level of miR-125b in the subject is reduced relative to a reference ratio of expression level of miR-342 to expression level of miR-125b at at least 1 time point, at least 2 time points, at least 3 time points, at least 4 time points, at least 5 time points, at least 6 time points, at least 7 time points, at least 8 time points, at least 9 time points, or at least 10 time points.

The herein disclosed methods may include a step of: (1) treating a subject for a head and neck cancer; (2) imaging a subject; or (3) a combination thereof, following: (1) predicting the subject has an increased likelihood of developing a head and neck cancer (2) diagnosing the subject with a head and neck cancer; (3) determining the presence of a head and neck cancer in the subject; (4) identifying the subject as eligible for a head and neck cancer; (5) predicting the subject has an increased likelihood of reoccurrence of a head and neck cancer; or (6) a combination thereof. Examples of imaging include performing a CT, PET, PET/CT, and MRI scan.

The herein disclosed methods that include a step of: (1) treating a subject for a head and neck cancer; (2) imaging a subject; or (3) a combination thereof, may be performed at periodic time points, for example, each day, each week, every two weeks, every three weeks, every four weeks, each month, every two months, every three months, every four months, every five months, every six months, and/or every year.

A subject may be: (1) treated for a head and neck cancer; (2) imaged; or (3) a combination thereof, when the subject has an expression level of miR-125b in the subject is elevated relative to a reference expression level of miR- 125b, or when the ratio of expression level of miR-342 to expression level of miR-125b in the subject is reduced relative to a reference ratio of expression level of miR-342 to expression level of miR-125b at at least 1 time point, at least 2 time points, at least 3 time points, at least 4 time points, at least 5 time points, at least 6 time points, at least 7 time points, at least 8 time points, at least 9 time points, or at least 10 time points.

Monitoring a subject undergoing treatment for a head and neck cancer refers to assessing the effectiveness of the head and neck cancer treatment. The: (1) number of measurements; (2) length of time between measurements; (3) length of time for the total assessment; or (4) a combination thereof, may vary depending on: (1) the type of head and neck cancer; (2) the stage of the head and neck cancer; (3) the type of head and neck cancer treatment; or (4) a combination thereof. The herein disclosed methods for monitoring a subject undergoing treatment for a head and neck cancer may be carried out at periodic time points, for example, each day, each week, every two weeks, every three weeks, every four weeks, each month, every two months, every three months, every four months, every five months, every six months, and/or every year that the subject is undergoing treatment for a head and neck cancer.

The progression of a head and neck cancer in a subject may be assessed as slowing when an expression level of miR-125b in the subject is decreased relative to an expression level of miR-125b measured at at least 1 earlier time point, at least 2 earlier time points, at least 3 earlier time points, at least 4 earlier time points, at least 5 earlier time points, at least 6 earlier time points, at least 7 earlier time points, at least 8 earlier time points, at least 9 earlier time points, or at least 10 earlier time points. The progression of a head and neck cancer in a subject may also be assessed as slowing when the ratio of expression level of miR-342 to expression level of miR-125b in the subject is elevated relative to a reference ratio of expression level of miR-342 to expression level of miR-125b measured at at least 1 earlier time point, at least 2 earlier time points, at least 3 earlier time points, at least 4 earlier time points, at least 5 earlier time points, at least 6 earlier time points, at least 7 earlier time points, at least 8 earlier time points, at least 9 earlier time points, or at least 10 earlier time points.

The herein disclosed methods for monitoring a subject undergoing treatment for a head and neck cancer may allow for an increase in the number of measurements compared to one or more known methods for monitoring a subject undergoing treatment for a head and neck cancer that do not use miR-125b or miR-342 and miR-125b, which may allow for a more accurate assessment of the effectiveness of the treatment and/or a more accurate assessment of the patient's health during treatment. The herein disclosed methods for monitoring a subject undergoing treatment for a head and neck cancer may allow for a shorter length of time between measurements compared to one or more known methods for monitoring a subject undergoing treatment for a head and neck cancer that do not use miR-125b or miR-342 and miR-125b, which may allow for an earlier assessment of the effectiveness of the treatment and therefore may reduce the subject's pain caused by extended ineffective treatment. The herein disclosed methods may allow for a shorter length of time for the total assessment compared to one or more known methods for monitoring a subject undergoing treatment for a head and neck cancer that do not use miR-125b or miR-342 and miR-125b, which may decrease the subject's discomfort during the assessment.

Probes to the herein disclosed miRNAs may be comprised in a kit. Probes refer to any chemical compound that is able to bind, directly or indirectly, to the herein disclosed miRNAs and detect or be detectable. In the context of the present disclosure, "binds" may refer to a "hybridization" reaction in which one or more nucleotides react to form a complex that is stabilized via hydrogen bonding between the bases of the nucleotide residues. Hybridization reactions can be performed under conditions of different "stringency". Relevant conditions include temperature, ionic strength, and the presence of additional solutes in the reaction mixture such as formamide. Conditions of increasing stringency are 30° C. in 10×SSC (0.15M NaCl, 15 mM citrate buffer); 40° C. in 6×SSC; 50° C. in 6×SSC 60 C. in 6×SSC, or at about 40° C. in 0.5×SSC, or at about 30° C. in 6×SSC containing 50% formamide. SDS and a source of fragmented DNA (such as salmon sperm) are typically also present during hybridization. Higher stringency requires higher minimum complementarity between hybridizing elements for a stable hybridization complex to form. See "Molecular Cloning: A Laboratory Manual", Second Edition (Sambrook, Fritsch & Maniatis, 1989). It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution.

The components of the kit may be packaged in one or more containers, for example, a vial, a test tube, a flask, a bottle, and a syringe. Each component of the kit may be packaged in a separate container or may be packaged with one or more components in the kit in the same container. The components of the kit may be packaged either in aqueous media or in lyophilized form. Optionally, the components of the kit may be contained in close confinement for commercial sale, for example, in a commercial package. The commercial package may comprise a container containing one or more probes to the herein described miRNAs and instructions directed to the use of the components of the container. In some examples according to the present disclosure, the commercial package is a plastic container.

Optionally, the kit may include components that preserve or maintain the probes, for example by protecting the probes from degradation.

Optionally, the kit may include instructions for employing the kit components. The instructions may include instructions for employing reagents that may be used in conjunction with the components of the kit but are not included in the kit.

In some examples according to the present disclosure, the kit comprises: (1) a probe for miR-342; (2) a probe for miR-125b; (3) a probe for miR-23; (4) an anticancer agent; or (5) a combination thereof.

EXAMPLES

Example 1—Materials and Methods

Serum Processing:

Serum samples were obtained from whole blood after allowing the blood to clot for 30 minutes and centrifuging at 1500 rcf for 15 minutes. The serum fraction was collected and then frozen at −80° C. until RNA extraction.

RNA Extraction:

Total RNA was extracted from 200 µL of serum using miRNeasy Mini Kit (Qiagen, Toronto, ON, Canada) according to manufacturer instructions, with the addition of 1.25 µL of MS2 carrier RNA (Roche Applied Science, Laval, QC, Canada) per 200 µL of serum added to the QIAzol Lysis Reagent prior to RNA purification. Purified RNA was resuspended in 50 µL of nuclease-free water and stored at −80° C. prior to assaying miRNA expression.

qRT-PCR:

RNA was quantified using a Qubit 3.0 (Thermo Fisher) using the RNA HS reagents. Reverse transcription was performed on 300ng of RNA using the TaqMan miRNA reverse transcription kits. A pre-amplification step was also included using the PreAmp Master Mix and custom pooled primers from Thermofisher. For the qRT-PCR step, Universal Master Mix II was used according to manufacturer's recommendations using the primers for hsa-miR-342-3p (Taqman MicroRNA Assay #2260), hsa-miR-125b-5p (Taqman MicroRNA Assay #449) and hsa-miR-23b-3p (Taqman MicroRNA Assay #400). A skilled person would understand how to design and create and/or purchase commercially prepared primers for hsa-miR-342-3p, hsa-miR-125b-5p, and hsa-miR-23b-3p. The authors used primers ordered from ThermoFisher: Primer for miR-342-3p catalogue #: 4427975 (www.thermofisher.com/order/qenome-database/details/microrna/002260?CID=&ICID=&subtvpe='): Primer for miR-125b catalogue #: 4427975 (www.thermofisher.com/order/qenome-database/details/microrna/000449?CID=&ICID=&subtvpe'): and Primer for miR-23b catalogue #: 4427975 (www.thermofisher.com/order/qenome-database/details/microrna/000400?CID=&ICID=&subtvpe='). Alternatively, a skilled person could use the SYBR based system from Exiqon or Qiagen.

Data Analysis:

Ct values for miRNAs that were not detected were set to the threshold of detection (37 Ct). The Ct value of each miRNA was subtracted from the Ct of the chosen normalizing miRNA, mir-23b, to obtain a normalized dCt value. The dCt values were then linearized using the formula CTlinear=2(−CT normalized). A classification algorithm was performed and identified the following equation that best classifies cancer and non-cancer individuals:

=([miR-125b-5p]*−0.308843)+([miR-342-3p]*0.010626)+0.178205

The equation provides an output value that is cross referenced against the clinical data reference from which a cut off value for making a diagnostic call has been determined based on optimal sensitivity and sensitivity of the training set.

Example 2—Biomarker Discovery

As part of the biomarker discovery process, we were able to select the most robust miRNA for internal normalization of serum samples, and we identified circulating miRNAs that were affected by hemolysis (and therefore not reliable biomarker candidates) [MacLellan, S. A., et al., Pre-profiling factors influencing serum microRNA levels. BMC Clin Pathol, 2014.14: p. 27]. These miRNAs were eliminated from any further analysis for this reason. In order to first identify the circulating miRNA signature, expression of 742 known miRNAs was undertaken using the Exiqon miRCURY LNA Universal RT miRNA PCR Human Panel I and II. Per LASSO analysis, 14 miRNAs were determined to be potentially relevant for sample classification. Analysis of these miRNAs with a different platform (Taqman qRT-PCR), and application of step-wise forward discriminant analysis, reduced the final biomarker signature to two miRNAs.

Example 3—Testing the Accuracy of the Biomarkers

ROC plots provide a statistical method to assess the diagnostic accuracy of a test (or biomarker) that has a continuous spectrum of test results. The ROC curve is a graphical display of the trade-offs of the true-positive rate (sensitivity) and false-positive rate (1−specificity) corresponding to all possible binary tests that can be formed from this continuous biomarker. Each classification rule, or cut-off level, generates a point on the graph. The closer the curve follows the left-hand border and then the top-border of the ROC space, the more accurate the test.

The closer the curve comes to the 45° diagonal of the ROC space, the less accurate the test. The traditional ROC curve arises when a continuous value is measured in each subject, and the classification is positive if the value is above a threshold. As the threshold varies, a new classification rule is created, and the resulting plot is a single curve. The optimal ROC curve is the line connecting the points highest and farthest to the left upper corner. The rationale for the optimal ROC curve is that it captures the trade-off between sensitivity and specificity over a continuous range. Further, in the ROC curve, the slope of the tangent line at a cut-point gives the LR for that value of the test.

Figure 2:
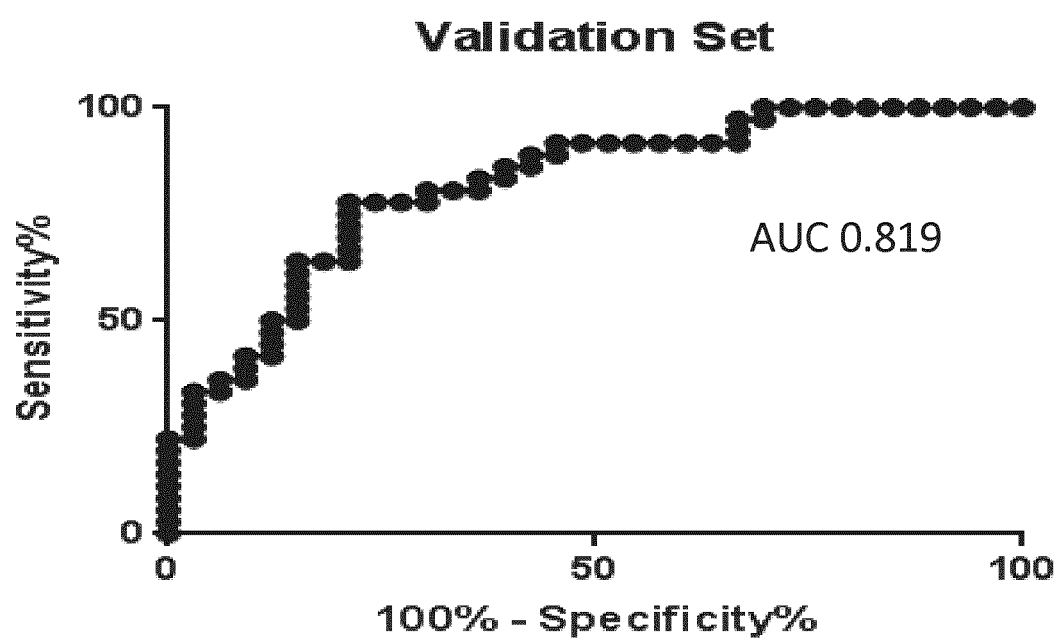
FIG. 2 is a graph illustrating a ROC for a validation data set of a classifier according to the present disclosure.

The two miRNA biomarkers identified in Example 2 were first derived on a training set of serum obtained from individuals with CIS or T1 (squamous cell carcinoma) disease compared to demographically matched controls (non-cancer). The test comprised of 76 samples included 33 control and 43 cancer samples. The training set ROC curve is shown in FIG. 1. A validation set was performed and supported the reproducibility to the training set. The test comprised of 69 samples including 33 control and 36 cancer samples. The validation set ROC curve is shown in FIG. 2. Minimal sensitivity and specificity cutoffs for a given biomarker is dependent on the clinical use. However, an AUC greater than 0.8 is generally believed to be a very good classifier. Since the classifier is built based on the training set samples, often the classifier will not perform at all or decreases in AUC values will be observed in the validation set. This is largely due to the population being tested and how well the training set represents the population as a whole. With the validation set, a slight but expected decrease in AUC was observed. However, the AUC remained above 0.8 providing confidence that the biomarker was a true classifier and not an artifact.

Figure 3:
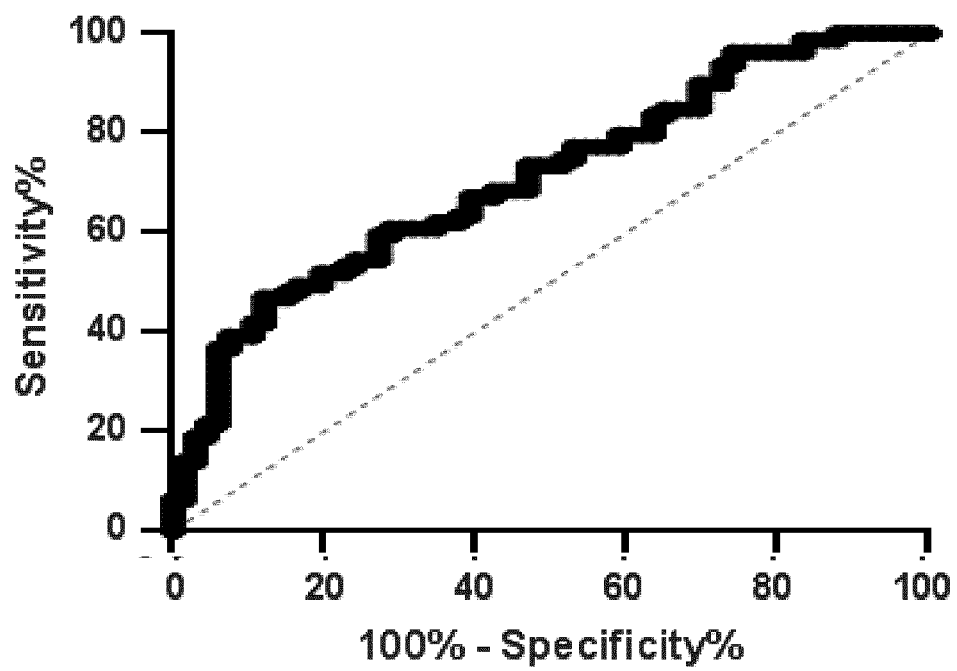
FIG. 3 is a graph illustrating a ROC using miR-125b according to the present disclosure.
Figure 4:
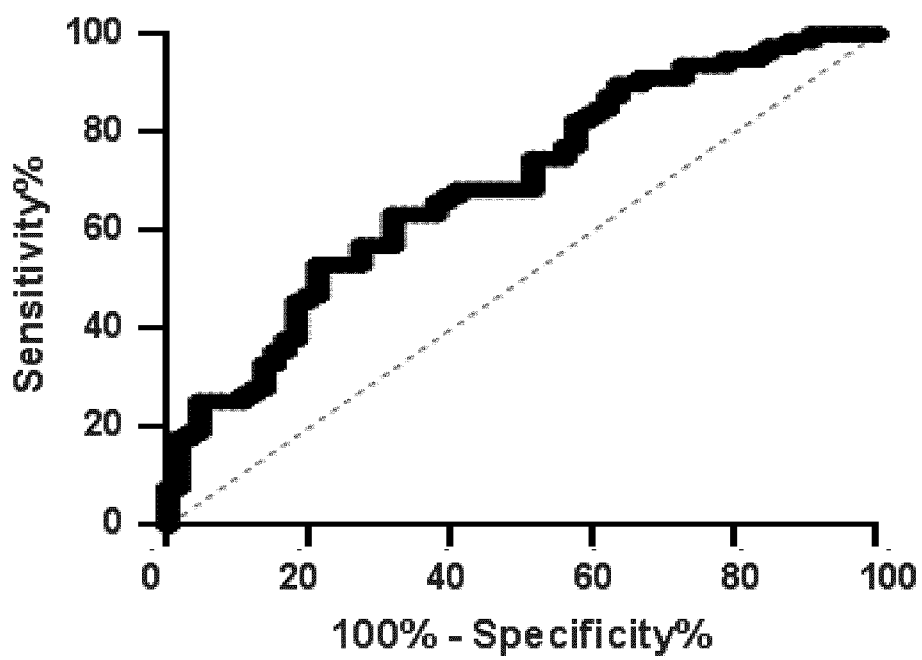
FIG. 4 is a graph illustrating a ROC using miR-342 according to the present disclosure.
Figure 5:
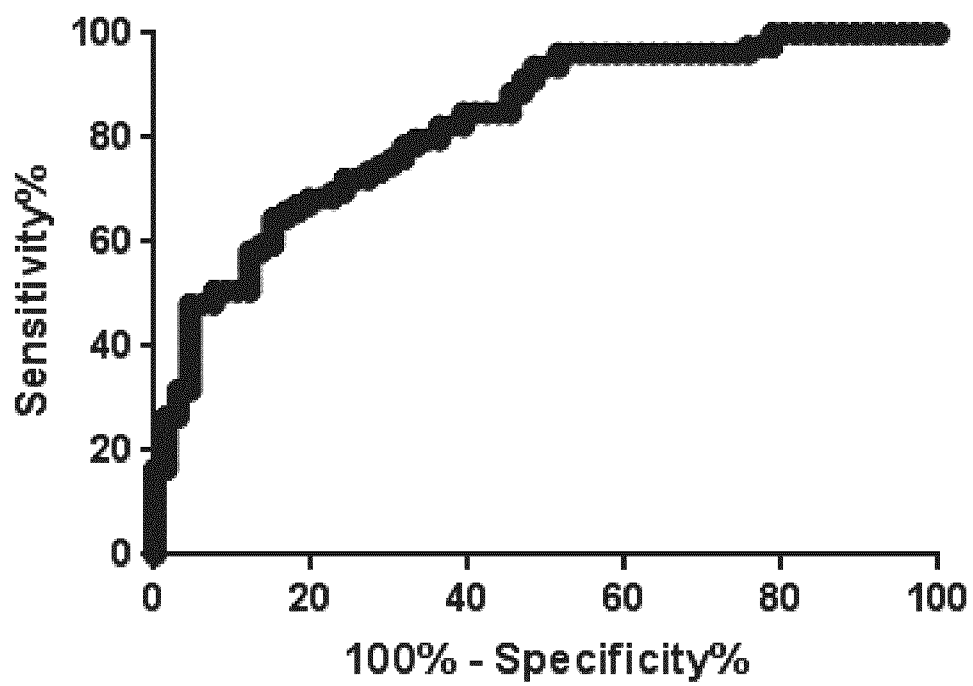
FIG. 5 is a graph illustrating a ROC using miR-125b and miR-342 according to the present disclosure.

We tested the classification strength of each miRNA biomarker identified in Example 2 (See FIGS. 3 and 4). We also tested the classification strength of the miRNA biomarkers together (See FIG. 5). miR-342 performed the worst with an AUC of 0.69. The AUC of miR-125 was 0.7. When using information from both miR-342 and miR-125, the AUC increased to over 0.8, which is within range of a useful biomarker.

All the cancer samples were compared to all of the control (non-cancer) samples, normalized, and linearized as per Example 1. The averages, max, and min for miR-342, miR-125b, and the ratio of miR-342 to miR-125b are provided in Table 1.

TABLE 1

Average values for normalized and linearized
Ct values. Ratios are defined as linearized
miR-342 Ct value/linearized miR-125b Ct value.

|  | lin125 | lin342 | ratio |
|---|---|---|---|
| AVG Cancer | 6.076696159 | 61.55890486 | 11.4851912 |
| MAX | 18.27226575 | 233.6451867 | 21.89352927 |
| MIN | 1.831953099 | 16.69678745 | 2.395822348 |
| AVG control | 2.369461086 | 157.8034987 | 67.85181527 |
| MAX | 6.694911016 | 510.8411043 | 231.2824218 |
| MIN | 1.124765563 | 60.31599642 | 35.65561437 |

Example 4—Testing the Clinical Usefulness of the Biomarkers

For the biomarkers identified in Example 2 to be clinically useful, a threshold value that defines a given group should be established. In order to determine the best thresholds for clinical use we combined data from training and validation data sets from Example 3 and added data from additional samples for a total of 238 samples (136 cancer samples and 102 non cancer samples). Taking the data as a whole we defined a threshold value that resulted in the best balance between sensitivity (70%) and specificity (68%). However, defining multiple thresholds (dividing the sample set into thirds) we noted a marked increase in PPV for the top third (PPV=89%). This would be of particular interest when screening for recurrent disease (See FIG. 6).

Example 5—Extracellular Vehicle (EV) Enrichment

Figure 7:
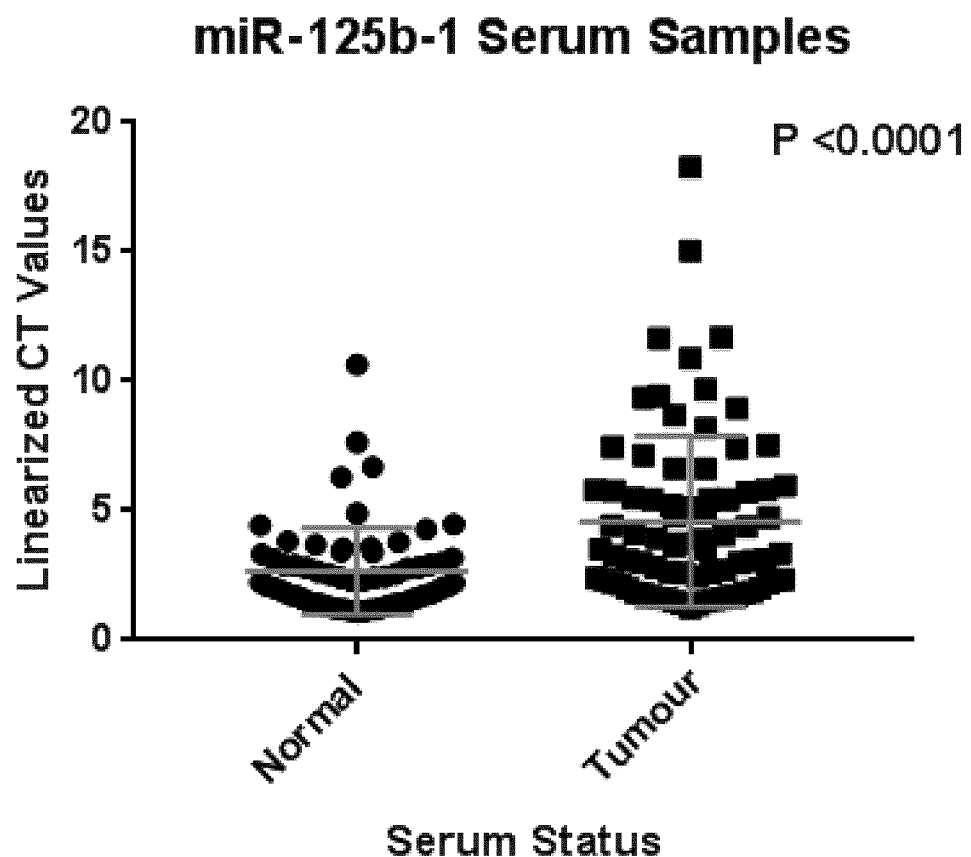
FIG. 7 is a graph illustrating normalized linearized Ct values for non-cancer control (Normal) and Tumor (head and neck) serum samples. miR-125b is more highly expressed in the tumor serum compared to normal controls.
Figure 8:
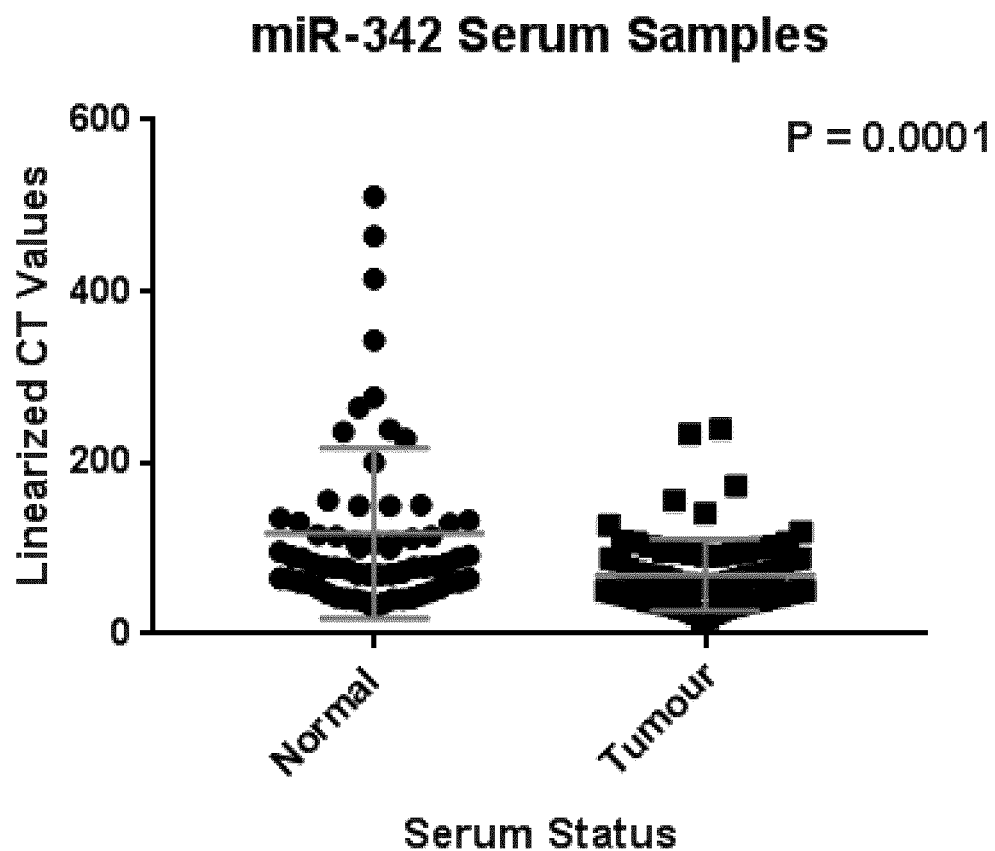
FIG. 8 is a graph illustrating normalized linearized Ct values for non-cancer control (Normal) and Tumor (head and neck) serum samples. miR-342 expression is downregulated in the tumor serum compared to normal controls.

With respect to the miRNAs that comprise the classifier outlined in Example 2, we found the average data values for miR-125 is more highly expressed in cancer serum compared to normal non-cancer control serum samples (See FIG. 7). We also found that the expression of miR-342 is decreased in cancer serum compared to non-cancer controls (See FIG. 8).

Example 6—Comparing the Ability of the Biomarkers to Detect Reoccurrence of Head and Neck Cancer Compared to Clinical Exam, i.e., Current Standard of Care Serum samples were taken from four patients at one time point between initial treatment and clinical detection of reoccurrence. The current standard of care for a clinical detection of reoccurrence is watchful waiting—patients are seen by the surgeon or treating oncologist every 3-6 months post treatment for 5 years. These follow up appointments consist of a clinical exam (i.e. a doctor will look and feel around for anything abnormal). The vast majority of recurrent cases are not diagnosed until the patient is experiencing new symptoms (pain, bleeding, etc.) If the patient has new symptoms, they will be sent for imaging (usually a CT scan) to try to locate and confirm the presence of the recurrence.

Figure 9:
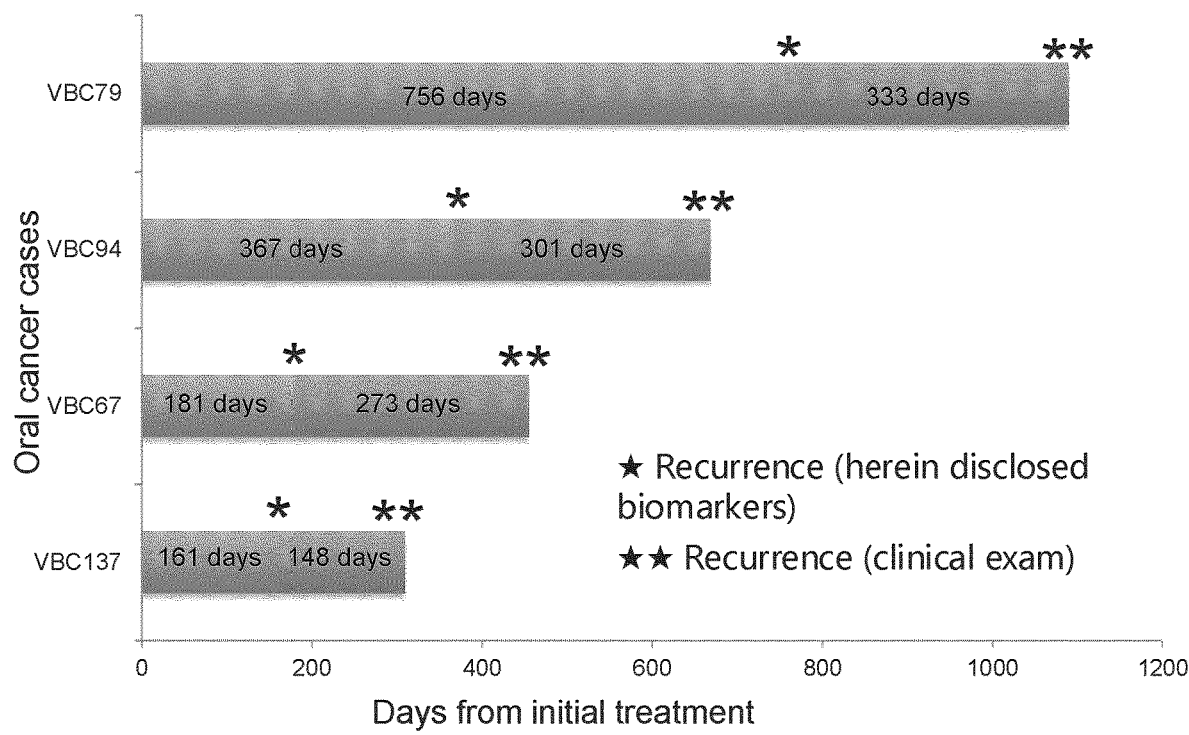
FIG. 9 is a bar graph illustrating how much sooner a classifier according to the present disclosure can detect recurrent disease compared to a standard clinical examination.

Across all cases, a positive result using the biomarkers outlined in Example 2 (signified as "★") was obtained an average 264 days prior to clinical detection of the disease (signified as "★★") (See FIG. 9). Reoccurrence was also positively confirmed at a later time point by clinical exam.

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A method comprising imaging the head and/or neck region of a subject having:
a ratio of measured expression level of miR-342 to measured expression level of miR-125b in a serum sample from the subject that is reduced relative to a reference ratio of expression level of miR-342 to expression level of miR-125b, wherein the measured expression level of miR-342 and miR-125b is normalized using a measured expression level of a normalizing miR in the serum sample,
wherein the imaging is CT, PET/CT, and/or MRI.

2. A method comprising:
a) measuring an expression level of miR-342 and miR-125b in a first serum sample from a subject undergoing treatment for an oral cavity cancer and/or oropharynx cancer at a first period of time;
b) measuring an expression level of a normalizing miR in the first serum sample at the first period of time and normalizing the measured expression levels of miR-342 and miR-125b of step a) using the measured expression level of the normalizing miR;
c) measuring an expression level of miR-342 and miR-125b in a second serum sample from the subject at a second period of time;
d) measuring an expression level of a normalizing miR in the second serum sample at the second period of time and normalizing the measured expression levels of miR-342 and miR-125b of step c) using the measured expression level of the normalizing miR;
e) calculating a reduced or no change in the ratio of normalized measured expression level of miR-342 to normalized measured expression level of miR-125b in step d) relative to a ratio of normalized measured expression level of miR-342 to normalized measured expression level of 125b in step b) to identify the subject as having a reoccurrence of an oral cavity cancer and/or oropharynx cancer or persistent oral cavity cancer and/or oropharynx cancer; and f) imaging the head and/or neck region of the subject, wherein the imaging is CT, PET/CT and/or MRI.

3. The method of claim 1, wherein the ratio of the normalized measured expression level of miR-342 to the normalized measured expression level of miR-125b is reduced relative to a reference ratio of expression level of miR-342 to expression level of miR-125b by at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, of at least about 60%, of at least about 70%, of at least about 80%, of at least about 90%, or 100%.

4. The method of claim 1, wherein the reference ratio of expression level of miR-342 to expression level of miR-125b is about 36.

5. The method of claim 1, wherein the reference ratio of expression level of miR-342 to expression level of miR-125b is about 22.

6. The method of claim 2, wherein the reduced ratio of the normalized measured expression level of miR-342 to the normalized measured expression level of miR-125b in step d) relative to the ratio of the normalized measured expression level of miR-342 to the normalized measured expression level of 125b in step b) is a reduction of at least about 0.5%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or 100%.

7. The method of claim 1 or 2, wherein the normalizing miR is miR-23b.

8. The method of claim 2, wherein measuring the expression levels comprises measuring the expression levels with qRT-PCR and normalizing comprises subtracting a Ct value of the measured expression level of miR-342 from a Ct value of the measured expression level of the normalizing miR and/or subtracting a Ct value of the measured expression level of miR-125b from a Ct value of the measured expression level of the normalizing miR.

9. The method of claim 2, wherein the oral cavity cancer and/or oropharynx cancer is head and neck squamous cell carcinoma (HNSCC).

10. The method of claim 1, wherein the expression levels were measured with qRT-PCR and normalized by subtracting a Ct value of the measured expression level of miR-342 from a Ct value of the measured expression level of the normalizing miR and/or subtracting a Ct value of the measured expression level of miR-125b from a Ct value of the measured expression level of the normalizing miR.

* * * * *

SEQUENCE LISTING

<160> NUMBER OF SEQ ID NOS: 5

<210> SEQ ID NO 1
<211> LENGTH: 21
<212> TYPE: RNA
<213> ORGANISM: Homo sapiens

<400> SEQUENCE: 1
aggggugcua ucugugauug a                                      21

<210> SEQ ID NO 2
<211> LENGTH: 23
<212> TYPE: RNA
<213> ORGANISM: Homo sapiens

<400> SEQUENCE: 2
ucucacacag aaaucgcacc cgu                                    23

<210> SEQ ID NO 3
<211> LENGTH: 99
<212> TYPE: RNA
<213> ORGANISM: Homo sapiens

<400> SEQUENCE: 3

```
gaaacugggc ucaaggugag gggugcuauc ugugauugag ggacaugguu aauggaauug        60
ucucacacag aaaucgcacc cgucaccuug gccuacuua                              99

<210> SEQ ID NO 4
<211> LENGTH: 22
<212> TYPE: RNA
<213> ORGANISM: Homo sapiens

<400> SEQUENCE: 4
ucccugagac ccuaacuugu ga                                                22

<210> SEQ ID NO 5
<211> LENGTH: 88
<212> TYPE: RNA
<213> ORGANISM: Homo sapiens

<400> SEQUENCE: 5
ugcgcuccuc ucagucccug agacccuaac uugugauguu uaccguuuaa auccacgggu        60
uaggcucuug ggagcugcga gucgugcu                                          88
```